United States Patent
Liu et al.

(10) Patent No.: US 9,693,995 B2
(45) Date of Patent: Jul. 4, 2017

(54) PHARMACEUTICAL COMPOSITION FOR TOPICAL ADMINISTRATION

(71) Applicant: Ziarco Pharma Ltd., Sandwich, Kent (GB)

(72) Inventors: Wai Leung Liu, Sandwich (GB); Lynn Purkins, Sandwich (GB); Michael Yeadon, Sandwich (GB)

(73) Assignee: Ziarco Pharma Limited, Sandwich, Kent (GB)

( * ) Notice: Subject to any disclaimer, the term of this patent is extended or adjusted under 35 U.S.C. 154(b) by 0 days.

(21) Appl. No.: 15/116,334

(22) PCT Filed: Feb. 4, 2015

(86) PCT No.: PCT/GB2015/050299
§ 371 (c)(1),
(2) Date: Aug. 3, 2016

(87) PCT Pub. No.: WO2015/118320
PCT Pub. Date: Aug. 13, 2015

(65) Prior Publication Data
US 2017/0007576 A1    Jan. 12, 2017

(30) Foreign Application Priority Data
Feb. 4, 2014   (GB) .................... 1401904.6

(51) Int. Cl.
| A61K 31/405 | (2006.01) |
| A61K 31/4045 | (2006.01) |
| A61K 9/00 | (2006.01) |
| A61K 45/06 | (2006.01) |
| A61K 47/10 | (2017.01) |
| A61K 9/06 | (2006.01) |
| A61K 9/107 | (2006.01) |

(52) U.S. Cl.
CPC ........ *A61K 31/4045* (2013.01); *A61K 9/0014* (2013.01); *A61K 9/06* (2013.01); *A61K 9/107* (2013.01); *A61K 45/06* (2013.01); *A61K 47/10* (2013.01)

(58) Field of Classification Search
CPC .................................................. C07D 209/08
USPC ....................................................... 514/415
See application file for complete search history.

(56) References Cited

FOREIGN PATENT DOCUMENTS

| EP | 2 468 270 A1 | 6/2012 |
| WO | WO 2006/128142 A2 | 11/2006 |
| WO | WO 2008/055136 A2 | 5/2008 |
| WO | WO 2008/055148 A2 | 5/2008 |

OTHER PUBLICATIONS

Burke, James R. et al., "BMS-229724 Is a Tight-Binding Inhibitor of Cytosolic Phospholipase A2 That Acts at the Lipid/Water Interface and Possesses Anti-Inflammatory Activity in Skin Inflammation Models", Journal of Pharmacology and Experimental Therpeutics, vol. 298, No. 1, 2001, pp. 376-385.
Finnin, B. et al., "Chapter 5: In Vitro Skin Permeation Methodology", in Transdermal and Topical Drug Delivery: Principles and Practice, First Edition, 2012: 85-108, Benson and Watkinson (Eds).
Hewson, C.A. et al., "Preclinical Evaluation of an Inhibitor of Cytosolic Phospholipase $A_2\alpha$ for the Treatment of Asthma", Journal of Pharmacology and Experimental Therpeutics, vol. 340, No. 3, 2011, pp. 656-665.
Lane, M., "Skin Penetration Enhancers", International Journal of Pharmaceutics, 2013, 447: 12-21.
Marshall, L. A. et al., "SB 203347, an Inhibitor of 14 kDa Phospholipase $A_2$, Alters Human Neutrophil Arachidonic Acid Release and Metabolism and Prolongs Survival in Murine Endotoxin Shock", Journal of Pharmacology and Experimental Therpeutics, vol. 274, No. 3, 1995, pp. 1254-1262.
McKew, J. C. et al., "Indole Cytosolic Phospholipase $A_2$ $\alpha$ Inhibitors: Discovery and in Vitro and in Vivo Characterization of 4-{3-[5-Chloro-2-(2-{[(3,4-dichlorobenzyl)sulfonyl]amino}ethyl)-1-(diphenylmethyl)-1H-indol-3-yl]propyl}benzoic acid, Efipladib", J. Med. Chem., 2008, 51, pp. 3388-3413.
Tibes, U. et al., "Phospholipase $A_2$ Inhibitors in Development", Exp. Opin. Invest. Drugs, 1997, 6(3): 279-298.

*Primary Examiner* — Raymond Henley, III
(74) *Attorney, Agent, or Firm* — Cooley LLP; Ivor R. Elrifi; Christina K. Stock

(57) ABSTRACT

The present invention relates to a pharmaceutical composition for topical administration comprising a compound of formula I, 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid:

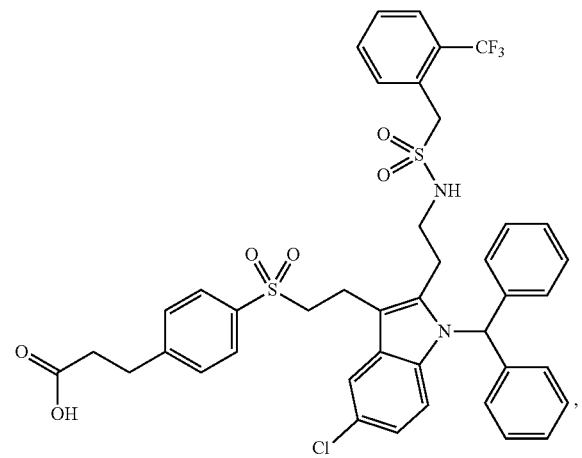

or pharmaceutically acceptable salts thereof; and to methods of treating inflammation comprising topical administration of a compositions comprising a compound of formula I.

17 Claims, 7 Drawing Sheets

PHARMACEUTICAL COMPOSITION FOR TOPICAL ADMINISTRATION

RELATED APPLICATIONS

This application is a U.S. National Phase application, filed under 35 U.S.C. §371(c), of International Application No. PCT/GB2015/050299, filed Feb. 4, 2015, which claims the benefit of and priority to GB Patent Application No. 1401904.6, filed Feb. 4, 2014, each of which are incorporated by reference herein in their entireties for all purposes.

FIELD OF INVENTION

The present invention relates to a pharmaceutical composition for topical administration comprising a compound of formula I, 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid or pharmaceutically acceptable salts thereof; and to methods of treating inflammation comprising topical administration of a composition comprising a compound of formula I.

BACKGROUND

Cytosolic phospholipase A2 (cPLA2), a member of the phospholipase A2 (PLA2) family, releases arachidonic acid from the phospholipid membrane and is the rate-limiting enzyme in the biosynthesis of prostaglandins (PGs), thromboxanes (Txs) and leukotrienes (LTs), all of which are implicated in the body's inflammatory response. Inhibition of this enzyme and other members of the PLA2 family is therefore a potential avenue for the amelioration of inflammatory diseases and conditions (Tibes & Friebe, Phospholipase A2 inhibitors in development. Expert Opin Investig Drugs. 1997 March; 6(3):279-98).

The compound 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid was identified as part of an effort to identify novel, high-potency inhibitors of cPLA2α (McKew et al. J Med Chem. 2008 Jun. 26; 51(12):3388-413). It may be manufactured as described in WO2006/128142, the contents of which are hereby incorporated by reference.

SUMMARY OF INVENTION

Inflammation of the skin is a symptom of many dermal diseases and conditions. Such conditions include, for example, atopic dermatitis, bullous disorders, collagenoses, psoriasis, psoriatic lesions, seborrheic dermatitis or contact dermatitis, eczema, urticaria, pruritus, rosacea, prurigo nodularis, hypertrophic scarring, keloid scar formation, scleroderma, Folliculitis keloidalis nuchae, Kawasaki Disease, Sjögren-Larsson Syndrome, Grover's disease, first, second, third and fourth degree burns, cutaneous mucinosis, solar keratosis, squamous cell carcinoma and melanoma. Treatment of inflammation in these conditions by agents targeting the PLA2 family is desirable.

Previously researchers have investigated inflammation treatments targeting the PLA2 family via the oral and pulmonary routes. In general, these treatments have focused on optimizing therapeutic agents for the oral route, which favours good oral bioavailability and long serum half-life when targeting PLA2 to treat inflammation. While still a design requirement, the potency of the agent is less critical when targeting the oral route since it is straightforward to increase the dose by incorporating more of the agent into the dosage form or by increasing the dosage frequency. Indeed, a common feature of prior art PLA2 inhibitors is their relatively low potency, for example, SB 203347 has been shown to fully inhibit PLA2 activity in acid extracted intact human neutrophil homogenate with an $IC_{50}$ of 4.7 µM (Marshall et al. J Pharmacol Exp Ther. 1995 September; 274(3):1254-62).

In general, the oral route is a suboptimal method to treat diseases of the skin. In particular, systemic administration (via the oral route or otherwise) carries with it the risk of side effects in tissues unconnected with the condition, for example gastrointestinal irritation and/or toxicity. Furthermore, compounds administered orally are subject to first pass metabolism via the liver. Instead, topical administration would frequently be the route of choice, if it could be achieved. The topical administration of a drug has many advantages in the treatment of a localized condition. Since the drug is made available at the site where it is required, an equivalent concentration of the drug circulating systemically is avoided. This can lessen or eliminate the side effects mentioned above.

Therefore, while cPLA2α inhibitors suitable for oral administration have been developed, there remains a need for effective cPLA2α inhibitors that may be administered topically.

Unfortunately, compounds optimized for oral administration are generally unsuitable for topical application, often due to the low potency discussed. For dermal administration, very high potency is required. It is also preferable that compound is cleared from the body quickly when not bound to its target. This set of properties allows the medicine to exert strong action on the skin only, and to avoid unwanted systemic effects.

Although desirable, formulation for dermal administration can be complex, since the drug is applied to the skin, classically considered a barrier to entry of xenobiotics. Previous research into topical drugs for application to the skin teaches that compounds with low molecular weight (<500 daltons) and moderate log P (0-3) are ideal for this use.

Surprisingly, the present inventors have found the compound of the present invention, an inhibitor of cPLA2α developed for oral administration, to be efficacious and well tolerated when delivered as part of a composition for topical administration. Until now, inhibitors of this class of enzyme have not been demonstrated to be useful via the topical route. This finding is particularly surprising given the relatively high molecular weight (823.35 daltons) of 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid and its high log P.

The compounds of the invention when formulated properly are, surprisingly and unexpectedly, shown to have anti-inflammatory action in an animal skin inflammation model and to penetrate into the deeper layers of human skin.

In the course of research leading to the present invention, it has been found that the compound of formula I can be applied to the skin as the active component of a topical composition and is available for penetration into the skin. Further, said compound has an anti-inflammatory action.

Therefore, the present invention provides a pharmaceutical composition for topical administration comprising a compound of formula I:

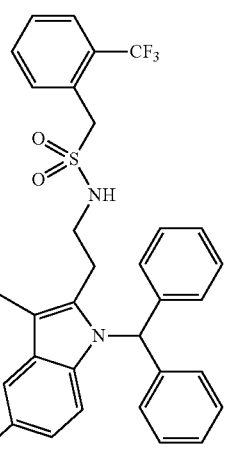

or pharmaceutically acceptable salts thereof and a pharmaceutically acceptable diluent or carrier.

Throughout the present application the compound of Formula (I) is also referred to as Compound I. It should be understood that wherever reference to Compound I is made, the use of a pharmaceutically acceptable salt of the compound is also contemplated.

Pharmaceutically acceptable salts of the compounds of Formula (I) having an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri lower alkylamine, for example ethyl-tert-butyl-, diethyl-, diisopropyl-, triethyl-, tributyl- or 5 dimethylpropylamine, or a mono-, di-, or trihydroxy lower alkylamine, for example mono-, di- or triethanolamine.

The term "topical administration" relates to the application of a substance directly to a body surface, such as the skin. In particularly preferred embodiments, the topical administration is epicutaneous, i.e., directly onto the surface of the skin. This may sometimes be referred to as dermal administration. The composition may be provided in any form suitable for topical administration, including but not limited to ointments, gels, creams, lotions, oil-in-water (o/w) emulsions, water-in-oil (w/o) emulsions, oil in water in oil (o/w/o) emulsions, water in oil in water (w/o/w) emulsions, microemulsions, foams, sprays, mousses, patches, powders, pastes, medicated plasters and the like, using well known techniques and excipients. Preferably the composition is provided in the form of a cream, ointment, lotion or gel. Most preferably the composition is provided in the form of a cream or an ointment.

Particularly preferred compositions (which may also be referred to herein as formulations) are described in Tables 3 to 7. The most preferred formulations include, but are not limited to:

Ointment O2 (Table 3)
Ointment O2X (Table 3)
Ointment O4v4 (Table 3)
Ointment O4v4E (Table 3)
Ointment O5v2 (Table 3)
Ointment O7 (Table 3)
Cream 7PE (Table 5)
Cream 9 (Table 5)
Gel 1V3 (Table 7)
Gel 4V3 (Table 7)
Emulsified Gel 1V2 (Table 7)

In preferred embodiments, the compound of formula I or pharmaceutically acceptable salt thereof is present at from about 0.01% to about 10% (w/w). More preferably the compound of formula I or pharmaceutically acceptable salt thereof is present at from about 0.3% to about 3%. In other preferred embodiments the compound of formula I or pharmaceutically acceptable salt thereof is present at about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10% (w/w).

The carrier may be a solvent in which the active component is soluble.

Suitable solvents include, but are not limited to water (about 0-about 25% w/w); alcohols (about 0-about 20% w/w) selected from monohydric alcohols having from 1 to 18 carbons, such as methanol, ethanol, propanol, isopropanol, butanol, hexanol, cetyl alcohol, stearyl alcohol, and the like; dihydric and polyhydric alcohols, such as propylene glycol, glycerol; hexanetriols, such as 1,2,6-hexanetriol, sorbitol, 1,3-butanediol, 2,3-butanediol, etc.; lower alkyl ethers of glycols having from 1 to 6 carbons such as the monomethyl or monoethyl ether of ethylene or diethylene or propylene or dipropylene glycol, propylene glycol or dipropylene glycol monomethyl ethers, diethylene glycol monoethyl ether, ethylene glycol monomethyl ether, etc; polyethylene glycols having molecular weights of from 100 to 8,000, preferably in the range 4,000; esters of aliphatic monobasic and dibasic acids having from 2 to 22 carbons and monohydric alcohols having from 1 to 20 carbons, di- and polyhydric alcohols having from 2 to 20 carbons, and sugar alcohols such as isopropyl myristate, isopropyl palmitate, myristyl myristate, cetyl stearate, methyl stearate, isopropyl sebacate, methyl sebacate, sucrose monolaurate, sucrose monostearate, and the like. Other suitable solvents include mannitol, xylitol, sorbitol and monohydric alcohols having from 1 to 6 carbons in the range of 0-20% (w/w), such as methanol, ethanol, propanol, isopropanol, butanol, or hexanol.

More specifically, the solvent may comprise a non-toxic glycol or glycol ether selected from the group consisting of propylene glycol, butylene glycol, diethylene glycol and diethylene glycol ether. Other preferred solvents include, but are not limited to, ethanol, deionized water, benzyl alcohol, PEG 400, dimethyl isosorbide (Arlasolve dmi), diethylene glycol monoethyl ether (Transcutol P), glycerin (glycerol), isopropyl myristate (IPM), isopropanol (isopropyl alcohol), octyldodecanol, phenoxyethanol, oleyl alcohol, mineral oil (liquid paraffin), Crodamol GTCC (caprylic/capric triglyceride or medium chain triglycerides), castor oil, isopropyl palmitate (IPP), propylene glycol dicaprylate/dicaprate and apricot kernel oil PEG-6 esters (Labrafil M1944CS).

The composition may also include a co-solvent, which may be selected from the list of solvents provided above. In particular, the co-solvent is selected from the group comprising of water, mannitol, xylitol, sorbitol and monohydric alcohols having from 1 to 6 carbons in the range of 0-20% (w/w), such as methanol, ethanol, propanol, isopropanol, butanol, or hexanol; and when another co-solvent is selected from one or more of the group consisting of propylene glycol (in the range 0-35% w/w), glycerol (in the range 0-10% w/w), polyethylene glycols such as PEG400 (in the range 0-80% w/w) or PEG4000 (or similar molecular weight agents in the class) (in the range 0-30% w/w).

Furthermore, two or more different solvents may be combined into solvent systems with desirable properties. Examples of suitable solvent systems are provided in Table 1:

TABLE 1

Examples of suitable solvent systems.

| Solvent systems | Composition (% w/w) |
|---|---|
| 1 | 85% PEG-400, 15% Arlasolve DMI |
| 2 | 75% PEG-400, 25% Transcutol P |
| 3 | 80% PEG-400, 20% propylene glycol |
| 4 | 20% EtOH, 55% PEG-400, 25% Transcutol P |
| 5 | 20% EtOH, 80% PEG-400 |
| 6 | 20% water, 55% PEG-400, 25% Transcutol P |
| 7 | 20% EtOH, 20% water, 2% benzyl alcohol, 33% PEG-400, 25% Transcutol P |
| 8 | 20% EtOH, 20% water, 33% PEG-400, 25% |

Where composition is in the form of an emulsion (oil-in-water (o/w), water-in-oil (w/o) oil in water in oil (o/w/o) and water in oil in water (w/o/w)), the composition may further comprise an emulsifier. This may be included to adjust the size of the droplets of oil in the oil phase, which may have a diameter of up to 200 µm, to a smaller size, typically in the range of 1-50 µm, thereby improving the cosmetic appearance of the composition. The emulsifier may suitably be a water-in-oil emulsifier, e. g. selected from the group consisting of water-in-oil emulsifiers such as, for example, polyoxyalkylene C12-20 alkyl ethers, such as polyoxyethylene-2-cetyl ether, polyoxyethylene-2-lauryl ether, polyoxyethylene-2-oleyl ether or polyoxyethylene-2-stearyl ether, polyoxyalkylene alkyl esters, sorbitan oleate, sorbitan isostearate, sorbitan sesquioleate, glycerol esters of isostearic acid and adipic acid, polyglyceryl-3-diisostearate and polyglyceryl-6-hexaricinoleate. The emulsifier may suitably be a oil-in-water emulsifier, e.g. selected from the group consisting of oil-in-water emulsifiers such as, for example, polyoxyalkylene C12-20 alkyl ethers and esters, such as polyoxyethylene-20-cetyl ether, polyoxyethylene-20-lauryl ether, polyoxyethylene-20-oleyl ether or polyoxyethylene-20-stearyl ether, polysorbate 20, polysorbate 60, polysorbate 80 and the like.

The composition of the present invention may be prepared in accordance with methods well known to the person skilled in the art of pharmaceutical formulation. The amount of the individual ingredients in the composition will, to some extent, depend on the concentration of the active component incorporated therein. The amount of active component in the composition may vary widely according to the severity of the condition to be treated, the age and condition of the patient and the discretion of the physician.

In addition to the above-mentioned ingredients, the present composition may include one or more additional ingredients such as:
1. other therapeutically active substances applied in the treatment of dermal inflammatory conditions, including:
   a. corticosteroids such as hydrocortisone;
   b. non-steroidal anti-inflammatories such as salicylic acid, salicylates, Vitamin D analogues such as calcipotriol (Dovonex), immunophilins, p38 kinase inhibitors, calcineurin inhibitors such as Tacrolimus and Pimecrolimus; and cannabinoids;
   c. vasomodulators such as alpha adrenoreceptor ligands; and
   d. topical anesthetics such as bupivacaine, chloroprocaine, dibucaine, ketamine and pramoxine.

2. anti-infectives such as:
   a. topical antibiotics such as clindamycin.
   b. antifungals
   c. antivirals Other suitable co-administrants are well known to those skilled in the art, including but not limited to:
1. Histamine $H_1$ receptor antagonists
2. Histamine $H_2$ receptor antagonists
3. Histamine $H_3$ receptor antagonists
4. Leukotriene antagonists, including antagonists of $LTB_4$, $LTC_4$, $LTD_4$, and $LTE_4$, for example Montelukast
5. Phosphodiesterase inhibitors, including PDE3 inhibitors, PDE4 inhibitors, PDE5 inhibitors, PDE7 inhibitors and inhibitors of two or more phosphodiesterases, such as dual PDE3/PDE4 inhibitors
6. neurotransmitter re-uptake inhibitors, in particular fluoxetine, sertraline, paroxetine, ziprasidone
7. 5-Lipoxygenase (5-LO) inhibitors or 5-lipoxygenase activating protein (FLAP) inhibitors
8. $\alpha_1$- and $\alpha_2$-adrenoceptor agonist vasoconstrictor sympathomimetic agents
9. Muscarinic $M_3$ receptor antagonists or anticholinergic agents
10. $\beta_2$-adrenoceptor agonists
11. Dual acting $\beta_2/M_3$ agents
12. Xanthines, such as theophylline and aminophylline
13. Non-steroidal anti-inflammatories, such as sodium cromoglycate and nedocromil sodium
14. Ketotifen
15. COX-1 inhibitors (NSAIDs) and COX-2 selective inhibitors
16. Oral, inhaled, intranasal and topical glucocorticosteroids
17. Monoclonal antibodies active against endogenous inflammatory entities
18. Anti-tumor necrosis factor (anti-TNF-$\alpha$) agents
19. Adhesion molecule inhibitors including VLA-4 antagonists
20. Kinin-$B_1$- and $B_2$-receptor antagonists
21. Immunosuppressive agents
22. Inhibitors of matrix metalloproteases (MMPs)
23. Tachykinin $NK_1$, $NK_2$ and $NK_3$ receptor antagonists
24. Elastase inhibitors
25. Adenosine A2a receptor agonists
26. Inhibitors of urokinase
27. Compounds that act on dopamine receptors, e. g. D2 agonists
28. Modulators of the NFκb pathway, e. g. IKK inhibitors
29. Agents that can be classed as mucolytics or antitussive agents
30. Antibiotics
31. Modulators of cytokine signaling pathways, such as p38 MAP kinase inhibitors, SYK kinase inhibitors or JAK kinase inhibitors
32. Modulators of the prostaglandin pathways, including inhibitors of H-PDGS and antagonists of DP-1 and CRTH2
33. Antagonists of chemokine receptors CXCR1 and CXCR2
34. Antagonists of chemokine receptors CCR3, CCR4 and CCR5
35. Inhibitors of cytosolic and soluble phospholipase $A_2$ (cPLA2 and sPLA2)
36. Inhibitors of phosphoinositide-3-kinase,
37. HDAC inhibitors,
38. p38 inhibitors and/or 39. CXCR2 antagonists.
40. Calcineurin inhibitors
41. Anti-interleukin 17 (anti-IL-17) agents
42. Anti-interleukin 4 receptor (anti-IL4R) agents
43. Anti-interleukin 31 (anti-IL-31) agents The effect the active agent or agents in any formulation may be enhanced by use of agents to enhance dermal penetration. Examples of suitable agents to enhance dermal penetration are disclosed at Int J Pharm. 2013 Apr. 15; 447(1-2):12-21 (incorporated herein by reference). Thus, the composition of the present invention may include one or more penetration enhancers. Penetration enhancers include but are not limited to 2-(2-Ethoxyethoxy)ethanol and dimethyl isosorbide in the range of 5-30% (w/w). Other non-limiting examples of penetration enhancers include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C8 diacids such as diisopropyl adipate; monoglycerides of C8-C22 fatty acids such as glyceryl monolaurate; tetrahydrofurfuryl alcohol polyethylene glycol ether; polyethylene glycol; propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; terpenes; macrocyclic enhancers such as macrocyclic ketones, for example, 3-methylcyclopentadecanone, 9-cycloheptadecen-1-one, cyclohexadecanone, and cyclopentadecanone; macrocyclic esters such as pentadecalactone.

The composition of the invention may include water, but it may also be substantially or totally free of water. Preferably, the water content of the composition is from about 0 to about 80% (w/w).

The present composition may also comprise other components commonly used in topical formulations, including but not limited to antioxidants (e.g. alpha-tocopherol, butylated hydroxytoluene, butylated hydroxyanisole), stabilizers, chelating agents, thickeners, softeners, lubricants, preservatives, emollients, pigments, fragrances, skin soothing agents, skin healing agents and skin conditioning agents such as urea, glycerol, allantoin or bisabolol.

The composition may also comprise a surfactant or emulsifier including, but not limited to, apricot kernel oil PEG-6 esters (Labrafil M1944CS), ceteareth-12 (Brij C20), caprylocaproyl macrogol-8 glycerides (Labrasol), cetostearyl alcohol, glycerol monostearate, lauroyl macrogol-6 glycerides (Labrafil M2130CS), macrogol 15 hydroxystearate, (polyoxyl 15 hydroxystearate), macrogol cetostearyl ether (cetomacrogol 1000), PEG-100 stearate (Myrj S100), polyoxyl 35 castor oil (macrogolglycerol ricinoleate), polyoxyl 40 hydrogenated castor oil, PEG-40 stearate (macrogol stearate, polyoxyl stearate), polysorbate 60 (Tween 60), polysorbate 80 (Tween 80), Span 60 (sorbitan monostearate), steareth-2 (Brij S2), steareth-20 (Brij S20), and stearic acid.

The composition may also include one or more viscosity-increasing agents. Viscosity-increasing agents include, but are not limited to polyvinylpyrrolidone, polyvinylpolypyrrolidone (crospovidone), methyl cellulose, hydroxypropyl cellulose (HPC), hydroxypropyl methylcellulose (hypromellose, HPMC), hydroxyethyl cellulose (HEC), xanthan gum, Carbopol (carbomer), and sodium hyaluronate (hyaluronic acid).

In a particularly preferred embodiment, the composition comprises:

(a) The compound of formula I;

(b) A solvent;

(c) A co-solvent;

(d) A penetration enhancer; and (e) Water.

In another aspect there is provided a pharmaceutical composition for topical administration comprising a compound of formula I:

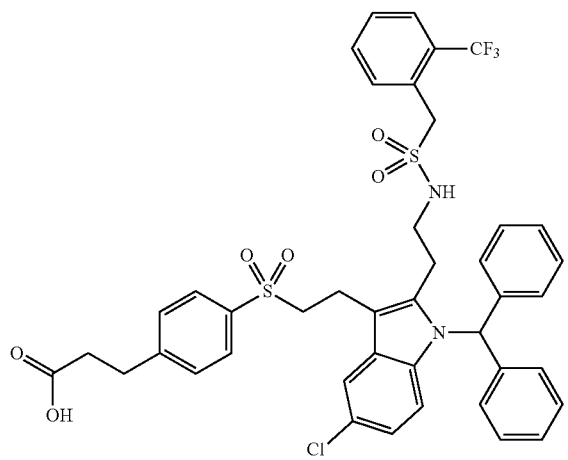 [SMILES: O=C(O)CCc1ccc(S(=O)(=O)CCc2c(CCNS(=O)(=O)Cc3ccccc3C(F)(F)F)n(C(c3ccccc3)c3ccccc3)c3ccc(Cl)cc23)cc1]

or pharmaceutically acceptable salts thereof and a pharmaceutically acceptable diluent or carrier, for use in therapy.

Preferably, therapy involves topical administration

In yet another aspect, there is provided a pharmaceutical composition for topical administration comprising a compound of formula I:

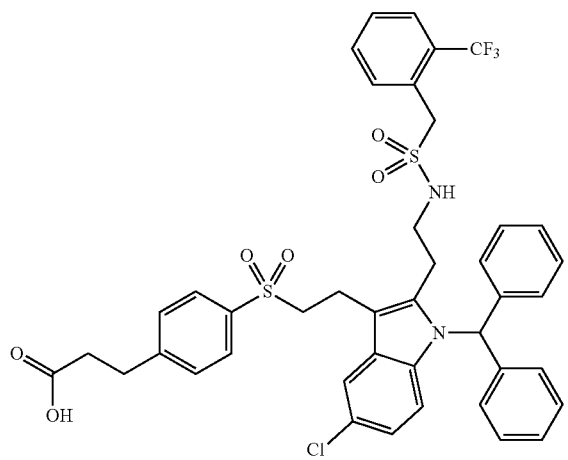 [SMILES: O=C(O)CCc1ccc(S(=O)(=O)CCc2c(CCNS(=O)(=O)Cc3ccccc3C(F)(F)F)n(C(c3ccccc3)c3ccccc3)c3ccc(Cl)cc23)cc1]

or pharmaceutically acceptable salts thereof and a pharmaceutically acceptable diluent or carrier, for use in treatment of dermal inflammatory diseases or conditions.

Also provided herein is the use of a compound of formula I:

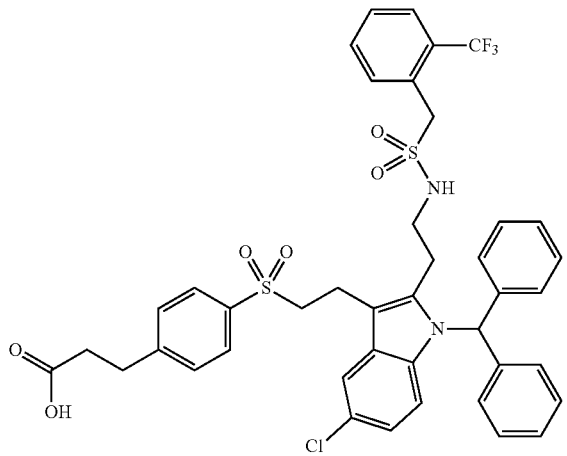 [SMILES: O=C(O)CCc1ccc(S(=O)(=O)CCc2c(CCNS(=O)(=O)Cc3ccccc3C(F)(F)F)n(C(c3ccccc3)c3ccccc3)c3ccc(Cl)cc23)cc1]

or pharmaceutically acceptable salts thereof in the manufacture of a medicament for the treatment of dermal inflammatory diseases or conditions The dermal inflammatory disease or condition to be treated is preferably a cytosolic phospholipase A2α-dependent or cytosolic phospholipase A2α-mediated disease or condition.

More preferably, the dermal inflammatory disease or condition is selected from the group comprising scarring, dermatitis, a proliferative disease or condition, a mast cell disease or condition, a burn or contact with an allergen and/or an irritant.

Yet more preferably, the dermal inflammatory disease or condition is selected from the group comprising atopic dermatitis, bullous disorders, collagenoses, psoriasis, psoriatic lesions, seborrheic dermatitis or contact dermatitis, eczema, urticaria, pruritus, rosacea, prurigo nodularis, hypertrophic scarring, keloid scar formation, scleroderma, Folliculitis keloidalis nuchae, Kawasaki Disease, Sjögren-Larsson Syndrome, Grover's disease, a first degree burn, a second degree burn, a third degree burn, a fourth degree burn, cutaneous mucinosis, solar keratosis, squamous cell carcinoma or melanoma, asteatotic eczema, discoid eczema, hand eczema, gravitational/varicose eczema, eczematous drug eruptions, lichen simplex, lichen sclerosus, lichen planus Irritant, allergic contact dermatitis, photoallergic/photoaggravated dermatitis, infective (secondary to bacterial/viral/fungal infection) dermatitis, pruritic diseases including those associated with chronic systemic disorders such as uremic pruritus, cholestatic pruritus, adult blaschkitis, aquadynia, aquagenic pruritus, balsam of Peru, biliary pruritus, brachioradial pruritus, drug-induced pruritus, hydroxyethyl starch-induced pruritus, itchy points, lichen simplex chronicus, neurodermatitis, prion pruritus, prurigo, prurigo pigmentosa, prurigo simplex, pruritus ani, pruritus scroti, pruritus vulvae, puncta pruritica, referred itch, renal pruritus, scalp pruritus, senile pruritus, xerotic eczema, itch associated with HIV infection, T-cell lymphoma, Sezary syndrome and mycosis fungoides.

Most preferably the dermal inflammatory disease or condition is psoriasis or atopic dermatitis.

In another aspect there is provided a method of treating inflammation and/or oedema in a patient in need thereof, the method comprising topical administration of a composition comprising a compound of formula I or a pharmaceutically acceptable salt to the area in need of treatment.

EXAMPLES

Figure 1:
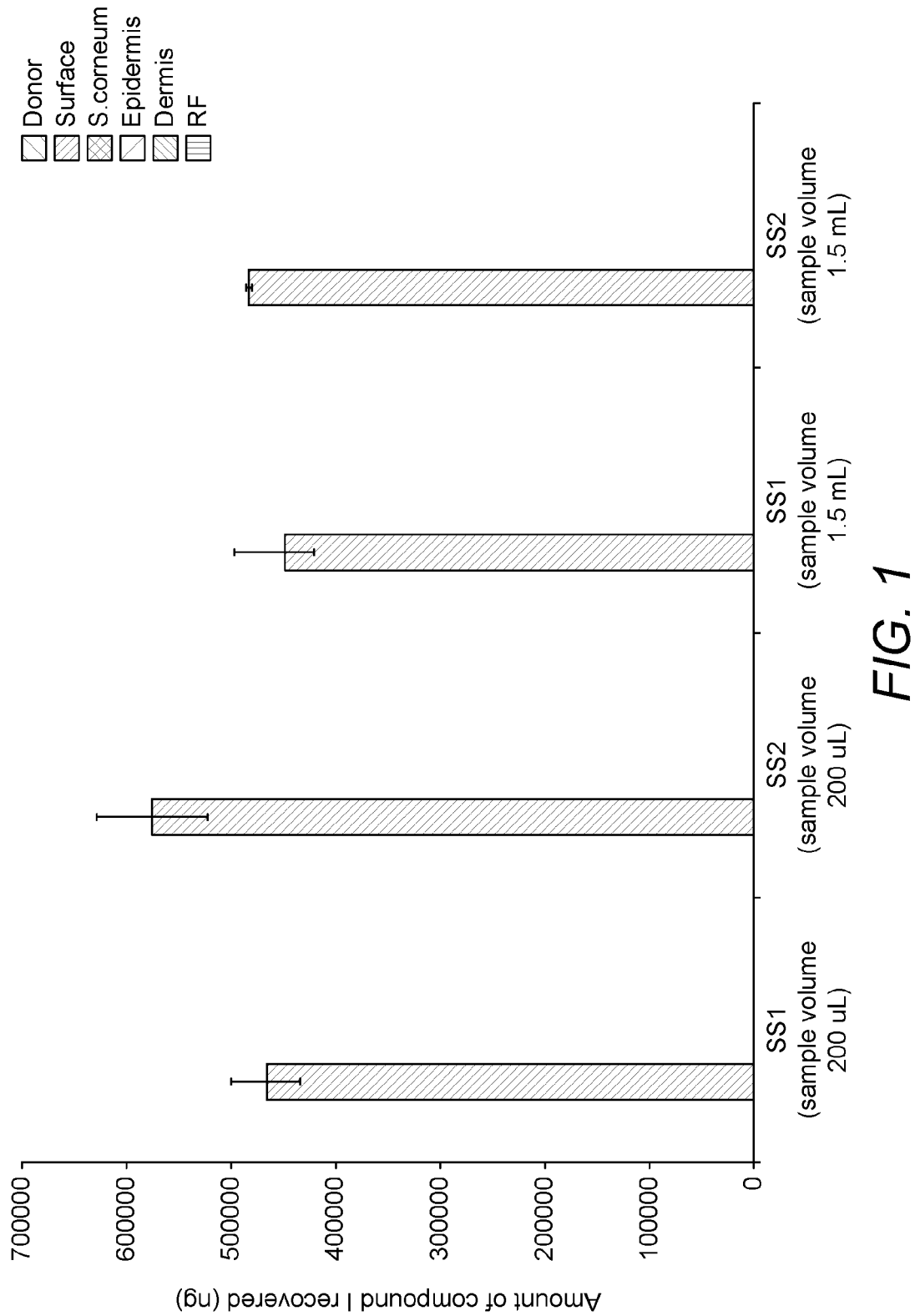
FIG. 1 shows the amount of Compound I (ng) recovered from the donor compartment, surface, Stratum corneum, epidermis, dermis and receiver fluid after the final time point (t=48 h) following the application of solvent systems SS1 and SS2 to dermatomed human skin. Each point represents the mean level of Compound I recovered with the error bars representing the range, n=2-3.

The present invention will be further understood by reference to the following examples.

Example 1

Manufacture of 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid The compound of formula I can be manufactured as described in WO2006/128142, the contents of which are hereby incorporated by reference. The following steps are carried out:

Step 1: 2-Bromo-4-chloroaniline (1.0 eq) was dissolved in CH$_2$Cl$_2$ (0.25 M), then triethylamine and trifluoroacetyl anhydride (1.1 eq each) were added. The resulting mixture was stirred at room temperature for 1 hour. The solvent was evaporated and the residue was purified by flash chromatography with CH$_2$Cl$_2$ as eluent to give the amide in 97% yield. m/z (M−H)$^-$ 300.0

Step 2: N-(2-Bromo-4-chlorophenyl)-2,2,2-trifluoroacetamide (Step 1, 1.0 eq) was mixed with 3-butyn-1-ol (2.0 eq), dichlorobis(triphenylphosphine)palladium(II) (2.5% eq), triethylamine (3.0 eq), CuI (5% eq) in DMF (0.2 M) in a sealed vessel under N$_2$ and heated to 120° C. for 4 hours. The reaction mixture was then diluted with ethyl acetate, washed with brine and dried over Na$_2$SO$_4$. Purification by flash column chromatography with 2% MeOH/CH$_2$Cl$_2$ afforded the alkyne in 67% yield. m/z (M−H)$^-$ 194.09

Step 3: 2-(5-Chloro-1H-indol-2-yl)ethanol (step 2, 1.0 eq) and imidazole (2.0 eq) were dissolved in DMF (0.3 M) at room temperature with stirring before tert-butylchlorodiphenylsilane (1.2 eq) was added. The resulting mixture was stirred overnight at room temperature before it was quenched with a saturated aqueous sodium bicarbonate solution and extracted with ethyl acetate. The organic phase was washed with water and brine and dried over $Na_2SO_4$. Purification by flash chromatography with $CH_2Cl_2$ as eluent afforded the silyl ether as a brown gum in over 90% yield. m/z (M−H)_ 433.0

Step 4: 2-({[tert-Butyl(diphenyl)silyl]oxy}ethyl)-5-chloro-1H-indole (Step 3, 1.0 eq) was dissolved in ether (0.4 M) and the solution was cooled to 0° C. Oxalyl chloride (1.2 eq) was added to the above cold solution with vigorous stirring. The reaction mixture was stirred at 0° C. for 1 hour before EtOH was added, followed by $NEt_3$. The resulting mixture was then diluted with more EtOH before it was poured into water and extracted with EtOAc. The organic phase washed with brine, dried over $Na_2SO_4$, and concentrated to give the ketoester as yellow solid in 70% yield. m/z (M−H)⁻ 533.0

Step 5: Ethyl [2-({[tert-butyl(diphenyl)silyl]oxy}ethyl)-5-chloro-1H-indol-3-yl](oxo)acetate (Step 4, 1 eq), $Ph_2CHBr$ (1.5 eq) and $Cs_2CO_3$ (1.5 eq) were mixed in dry acetonitrile (0.1 M). The mixture was heated to reflux for 2 hours. The reaction mixture was cooled to room temperature, diluted with water and extracted with EtOAc. The organic phase was concentrated and the residue was chromatographed with $CH_2Cl_2$ as eluent to give the N-benzhydryl indole as an orange gum in 45% yield. m/z (M+H)⁺ 701.3

Step 6: To a solution of ethyl [1-benzhydryl-2-({[tert-butyl(diphenyl)silyl]oxy}ethyl)-5-chloro-1H-indol-3-yl](oxo)acetate (Step 5, 1 eq) in THF (0.1 M) was added $BH_3.Me_2S$ (2M in THF) (2 eq). The resulting mixture was heated to reflux overnight under $N_2$. The reaction mixture was cooled to room temperature, then quenched slowly with 1N NaOH, extracted with EtOAc, and washed with brine. Concentration afforded the alcohol in 65% yield. m/z (M+H)⁺ 645.0

Step 7: To a solution of 2-[1-benzhydryl-2-({[tert-butyl(diphenyl)silyl]oxy}ethyl)-5-chloro-1H-indol-3-yl]ethanol (Step 6, 1 eq) in $CH_2Cl_2$ (0.08M) was added 1,3-bis(diphenylphosphino)-propane (DPPP, 0.75 eq). The solution was cooled to 0° C. under $N_2$, then $CBr_4$ (1.25 eq) was added. The reaction mixture was allowed to return to room temperature over 2 h. The solvent was evaporated, and the residue was purified using a short silica gel column with $CH_2Cl_2$ as eluent to give the bromide in quantitative yield. m/z (M+H)⁺ 708.0

Step 8: 1-Benzhydryl-3-(2-bromoethyl)-2-({[tert-butyl(diphenyl)silyl]oxy}ethyl)-5-chloro-1H-indole (Step 7, 1 eq) was mixed with methyl-3-(4-mercaptolphenyl)propionate (1.5 eq) and $K_2CO_3$ (1.5 eq) in DMF (0.1 M). The resulting mixture was stirred at room temperature under $N_2$ for 2 h, then diluted with water and extracted with EtOAc. The organic extract was washed with brine, concentrated, and purified by flash chromatography ($CH_2Cl_2$ as eluent) to give the thioether as a brownish gum in 80% yield. m/z (M+H) 823.0

Step 9: Methyl 3-[4-({2-[1-benzhydryl-2-({[tert-butyl(diphenyl)silyl]oxy}ethyl)-5-chloro-1H-indol-3-yl]ethyl}sulfanyl)phenyl]propanoate (Step 8, 1 eq) was dissolved in acetonitrile (0.1 M), then molecular sieves (powder, 4 A,) and 4-methylmorpholine N-oxide (NMO) (4 eq) were added under $N_2$. After 5 min, n-$Pr_4NRuO_4$ (TPAP) (5% eq) was added. The resulting mixture was heated at 40° C. for 1.5 h. The mixture was concentrated and the residue was purified by flash chromatography with $CH_2Cl_2$, then 1% EtOAc/$CH_2Cl_2$ as eluent to give the sulfone as a white foam in 44% yield. m/z (M+H)⁺ 855.1

Step 10: Methyl 3-(4-{2-[1-benzhydryl-2-({[tert-butyl(diphenyl)silyl]oxy}ethyl)-5-chloro-1H-indol-3-yl]ethoxy}phenyl)propanoate (Step 9, 1 eq) was dissolved in THF (0.1 M) and cooled to 0° C. then treated with $nBu_4NF$ (1 M in THF) (1.2 eq). The resulting mixture was stirred at 0° C. for 5 min, then warmed to room temperature and stirred for 30 min. The solvent was evaporated and the residue was purified by flash chromatography with EtOAc/$CH_2Cl_2$ (1:9 to 1:4) as eluent to give the alcohol as a white foam in 90% yield. m/z (M+H)⁺ 616.20

Step 11: Methyl 3-[4-{2-[1-benzhydryl-5-chloro-2-(hydroxyethyl)-1H-indol-3-yl]ethyl}-sulfonyl)phenyl] propanoate (Step 10, 1 eq) in $CH_2Cl_2$ (0.02 M) was treated at 0° C. with $MeSO_2Cl$ (2.0 eq) and $Et_3N$ (2.5 eq) and stirred for 1 hour. The ice-bath was removed and the reaction mixture was stirred for 1 hour at room temperature before it was diluted with $CH_2Cl_2$, washed with $NaH_2PO_4$, brine and dried over $Na_2SO_4$. Evaporation of the solvent afforded the mesylate in quantitative yield. m/z (M+H)⁺ 695.0

Step 12: Methyl 3-(4-{[2-(1-benzhydryl-5-chloro-2-{2-[(methylsulfonyl)oxy]ethyl}-1H-indol-3-yl)ethyl]sulfonyl}phenyl)propanoate (Step 11, 1.0 eq) was dissolved in DMF (0.03 M) and treated with NaN3 (3.0 eq). The resulting mixture was heated to 60° C. and stirred for 2 hours, then cooled to room temperature, diluted with water, extracted with ethyl acetate, washed with brine and dried with $Na_2SO_4$. Evaporation of solvent afforded the azide in quantitative yield, m/z (M+H)⁺ 641.1

Step 13: Methyl 3-[4-({2-[2-(2-azidoethyl)-1-benzhydryl-5-chloro-1H-indol-3-yl]ethyl}sulfonyl)phenyl]propanoate (Step 12, 1 eq) was dissolved in THF (0.1 M), and treated with triphenylphosphine (1.1 eq). After 2 days water was added, and the mixture was stirred overnight, concentrated, and purified by flash chromatography using 4% MeOH:$CH_2Cl_2$ as eluent to give the amine in 71% yield. m/z (M+H)⁺ 615.2

Step 14: To a suspension of (2-trifluoromethylphenyl)methanesulfonic acid (20.3 g, 84 mmol) in THF (1.9 L) and DMF (5.0 mL) at −20° C. was added oxalyl chloride (44.7 mL, 0.5 mol) slowly dropwise over 1 hr. The bath temperature was maintained below 0° C. for 4 h, at which point the reaction was evaporated to a volume of ~250 mL and diluted with 500 mL of ethyl acetate. This solution was washed with brine in a separatory funnel and dried over magnesium sulfate. The solution was then evaporated to a brown oil. This oil was taken up in 500 mL of pet ether) (30-50°) and heated with a heat gun until the oil went into solution. The solution was then placed into a dry-ice acetone bath to cool resulting in formation of a white crystalline material. This material was collected via filtration and dried to afford 19 g (85%) of (2-trifluoromethylphenyl)methanesulfonyl chloride as a white solid.

Step 15: To ethyl 3-[4-({2-[2-(2-aminoethyl)-1-benzhydryl-5-chloro-1H-indol-3-yl]ethyl}sulfonyl)phenyl]propanoate (Step 14, 200 mg, 0.32 mmol) and sat. $NaHCO_3$ (0.14 M) in $CH_2Cl_2$ (0.07 M) was added (2-trifluoromethylphenyl)methanesulfonyl chloride (Step 14, 110 mg, 0.42 mmol). After 16 h the mixture was poured into saturated sodium bicarbonate and extracted with CH2Cl2. The combined organic phase was washed with brine, dried over sodium sulphate and purified by column chromatography to afford 250 mg of the sulfonamide, a pale yellow foam, in 93% yield. ¹HNMR (400 MHz, $CDCl_3$) δ 1.23 (t, J=I.2 Hz, 3H), 2.62-2.71 (m, 2H), 2.76-2.93 (m, 4H), 2.98-3.17 (m, 4H), 3.27-3.38 (m, 2H), 4.11 (q, J=7.2 Hz, 2H), 4.35 (s, 2H), 4.57 (t, J=5.3 Hz, 1H), 6.43 (d, J=9.1 Hz, 1H), 6.77 (dd, J=8.8, 2.0 Hz, 1H), 6.81 (s, 1H), 7.18 (d, J=2.0 Hz, 1H), 7.24-7.35 (m, 10H), 7.41 (d, J=8.6 Hz, 3H), 7.49 (t, J=8.3 Hz, 1H), 7.60-7.77 (m, 2H), 7.88 (d, J=8.6 Hz, 2H).

Step 16: The resulting sulfonamide ester (220 mg, 0.26 mmol) was hydrolyzed by stirring with 1N NaOH (5 equiv) in THF (0.07M) and enough MeOH to produce a clear solution. The reaction was monitored by TLC (10% MeOH—$CH_2Cl_2$) for the disappearance of starting material. When the reaction was complete, mixture was concentrated, diluted with $H_2O$, and acidified to pH 2-4 using 1M HCl. The aqueous phase was extracted with EtOAc and the organic phase was washed with brine, dried over sodium sulphate, and concentrated to afford 200 mg (92%) of 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid, a white foam. $^1$HNMR (400 MHz, DMSO-$d_6$) δ 2.65 (t, J=7.6 Hz, 2H), 2.91-3.13 (m, 8H), 3.60 (dd, J=9.7, 5.4 Hz1 2H), 4.46 (s, 2H), 6.48 (d, J=8.8 Hz, 1H), 6.83 (dd, J=8.7, 2.1 Hz, 1H), 7.05-7.16 (m, 5H), 7.19 (d, J=2.3 Hz, 1H), 7.33-7.47 (m, 6H), 7.53-7.72 (m, 6H), 7.80 (d, J=7.6 Hz, 1H), 7.94 (d, J=8.3 Hz, 2H), 12.26 (s, 1H); HRMS: calcd for $C_{42}H_{38}ClF_3N_2O_6S_2$+H+, 823.18847; found (ESI-FTMS, [M+H]$^{1+}$), 823.1887; HPLC purity $H_2O/CH_3CN$: 100%, $H_2O$MeOH: 100%.

Example 2 'Proof of Concept' In Vitro Drug Permeation and Penetration Experiment Commonly, in vitro skin permeation experiments involve the use of a diffusion cell designed to mimic the physiological and anatomical conditions of skin in situ. The model used in this experiment was the Franz diffusion cell (Finnin et al. Topical and Transdermal Drug Delivery 2012: 85-100, Benson and Watkinson (Eds), incorporated herein by reference). Skin prepared as described below was positioned between the two halves of the cell with the Stratum corneum facing the donor compartment allowing for drug application. The aim of the work was to compare the drug concentrations permeating into and across dermatomed human skin when applied from different formulations/solvent systems. Where possible, the method was performed in accordance with OECD 428 guidelines.

Skin Preparation

Human skin from cosmetic reduction surgery was used. Subcutaneous fat was removed mechanically and the skin was dermatomed to a thickness of 400±100 μm using a Nouvag cutter.

Small Scale Skin Permeation Investigation

The feasibility experiment was performed as follows:

Preparation of the Franz Cells (i) Franz diffusion cells, with an average surface area of approximately 0.6 cm$^2$ and a volume of approximately 2.0 mL were employed.

(ii) Skin (prepared as described above) was mounted between the donor and receiver compartments and the cells were sealed together using Parafilm and clips.

(iii) To check the skin integrity the donor and receiver chambers were filled with PBS solution (prepared by dissolving 1 PBS tablet in 100 mL of water) and a small magnetic follower was placed in the receiver compartment.

(iv) Cells were equilibrated in a waterbath ensuring a membrane temperature of 32° C. for 30 min (waterbath temperature of 37° C.).

(v) The resistance of the skin in each Franz cell was measured using the LCR 6401 Databridge.

(vi) The electrodes were placed in the receiver compartment through the sampling arm and the donor chamber.

(vii) The LCR was set at 100 Hz and set to 'R' for resistance.

(viii) Cells with a resistance below the acceptable limits were discarded and remounted. Acceptable limits are defined according to the measurement of controls for dermatomed skin, where the skin has been deliberately perturbed. Cells with greater than twice the resistance (KΩ) of the control were considered acceptable and selected for the Franz cell permeation experiment.

(ix) Following skin integrity testing the receiver compartment of acceptable cells was filled with receiver fluid. Each cell was then equilibrated to ensure a surface temperature of 32° C. (external skin surface temperature) for at least 30 min prior to dosing (waterbath temperature of 37° C.).

(x) An additional Franz cell (per skin donor) was also mounted but not dosed (to act as a blank) to assess interference with sample quantification.

Dosing of Test Solvent Systems and Sampling Procedure

Two solvent systems were selected for a small scale in vitro drug permeation study and was dosed as described below:

(i) The cells were assembled as described above.

(ii) Nine cells were assembled. Two solvent system (n=3), respective placebo solvent system (n=1) and a blank cell (n=1) were assessed during the feasibility experiment.

(iii) The selected solvent systems (6 mg) were applied directly to the surface of the skin with a positive displacement pipette (resulting in a dose of approximately 10 mg/cm$^2$). The pipette was verified for the amount dispensed prior to dosing to ensure reproducibility of dose. The verification of the amount dispensed was performed by weighing 6 replicates into a glass vial. Weights and volumes applied (to ensure a 6 mg dose) were recorded.

(iv) Receiver fluid (200 μL) was removed at the following time points t=0, 1, 2, 4, 6, 24, 30 and 48 h. Each sample was split into 2×LCMS vials (100 μL per vial) where one was spiked with internal standard (1:1) and analyzed using LC-MS/MS. The second vial was stored at −20° C. as a back-up.

(v) Fresh pre-warmed receiver fluid (200 μL) was used to replace the receiver fluid removed at each time point.

(vi) Following the 48 h time point, Compound I was recovered from the Franz cell as described below.

Penetration Investigation

Following completion of the permeation experiment, quantification of residual Compound I from the donor chamber, on the surface of the skin, Stratum corneum, epidermis and partial dermis was performed using the following procedure:

Recovery from Donor Chamber (i) Three cotton swabs were used to recover Compound I from the donor chamber.

(ii) After dismantling the Franz cell one of the dry cotton wool swabs was used to remove all residual solvent from all the internal surfaces of the donor chamber and the swab placed into a 7 mL vial.

(iii) A second swab was then immersed into the extraction fluid and then used to swab the internal surface of the Franz cell, this swab was then placed into the vial containing the first swab.

(iv) The final swab was used dry to swab the inside of the Franz cell and then placed into the glass vial containing the two other swabs.
(v) Using a pipette 2 mL of extraction fluid was added to the glass vial containing the cotton swabs.
(vi) The vials were shaken on an orbital shaker at ambient temperature for 16-20 h.
(vii) Following the extraction procedure, the extraction solvent system was removed from the vials and centrifuged at 13,000 RPM (16,060 g-force) for 10 min using a Heraeus Labofuge pico centrifuge to remove un-dissolved materials and particulates.
(viii) The supernatant was split into 2 aliquots (100 μL in vial one and the remainder in the second vial), where vial one was spiked with internal standard (1:1) and analyzed using LC-MS/MS. The second vial was stored at −20° C. as a back-up Recovery from Upper Surface of the Skin
(i) Three cotton swabs were used to recover Compound I from the surface of the skin.
(ii) After dismantling the donor chamber from the Franz cell one of the dry cotton wool swabs was used to remove all of the residue solvent from the surface of the skin and the swab placed into a 7 mL vial.
(iii) A second swab was then immersed into the extraction solvent and used to swab the surface of the skin, this swab was then placed into the vial containing the wash solvent and the first swab.
(iv) The final swab was used dry to swab the surface of the skin and then placed into the glass vial containing the two other swabs.
(v) An initial tape strip from the surface of the skin was also placed in with the cotton wool swabs from Step (iv)
(vi) Steps (v)-(viii) from the method for recovery from the donor chamber were performed to complete the recovery of Compound I from the surface of the skin.

Recovery from the Stratum Corneum
(i) Up to 5 tapes strips were removed from the surface of the skin to separate the Stratum corneum from the epidermis and were placed in a 7 mL vial.
(ii) Steps (v)-(viii) from the method for recovery from the donor chamber were performed to complete the recovery of Compound I from the Stratum corneum.

Method for Separation and Recovery from Epidermal Membrane and Partial Dermis

The remaining epidermis and partial dermis was processed as follows:
(i) The epidermis and dermis were placed into an incubator at 60° C. for 2 min.
(ii) The epidermis and dermis were then removed from the incubator and manually separated using gloved hands.
(iii) The epidermal and dermal layers were placed into individual Precellys 24 homogeniser vials and 1 mL of extraction solvent was added.
(iv) The Precellys vial from Step (iii) was placed in the Precellys 24 and the contents homogenized at 5,800 RPM for 2×20 s at 2-8° C.
(v) The contents of the Precellys vial from Step (iv) were emptied into a 7 mL glass vial.
(vi) Extraction diluent (1 mL) were added to the empty Precellys vial from Step (v) and the vial vortex mixed for ca. 30 s, the contents were then emptied into the glass vial from Step (v).
(vii) Steps (vi)-(viii) from the method for recovery from the donor chamber were performed to complete the recovery of Compound I from the epidermis and dermis.

Full Scale Permeation and Penetration Study

The full scale in vitro drug permeation and penetration experiment was performed as described in relation to the small scale experiments, with the following modifications:
(i) Two solvent systems, with Compound I at close to saturation, were investigated: one with penetration enhancers (n=4 active, n=1 placebo) and one without penetration enhancers (n=4 active, n=1 placebo)
(ii) Skin from 3 donors was used, i.e. a total of 33 cells (n=12 cells per active, n=3 cells per placebo per formulation and n=3 cell as a blank per skin donor).

Data Analysis

The data analysis and statistical comparison of samples generated during the in vitro skin permeation experiment was performed as follows:
(i) The concentration (ng/mL) of Compound I detected in each sample was quantified from the calibration standards analyzed at the same time on the LC-MS/MS.
(ii) The total amount (ng) of Compound I per volume sampled was calculated (total amount/volume sampled=ng/mL×volume sampled).
(iii) The total amount (ng) of Compound I recovered at each time point was then calculated (total amount=ng/mL×total volume of each Franz cell).
(iv) The cumulative amount (ng) of Compound I was calculated by adding the total amount (ng, Step (iii)) at each time point with the total amount withdrawn (ng) from each of the previous time points (Step (ii)).
(v) The cumulative amount per unit area of Compound I (ng/cm2) was calculated by dividing the cumulative amount (ng, Step (iv)) by the diffusion area (ng/cm2=cumulative amount (ng)/diffusion area).
(vi) Any outliers were rejected according to internal procedures, however all data were reported
(vii) Flux rates (where possible) and penetration were calculated from the Compound I concentrations measured in the receiver fluid over time and concentration recovered from the dermis, respectively.

Identification of Outliers

Suspected outliers in the permeation/penetration experiment were confirmed and eliminated from further data analysis if their permeation data exceeded the limits defined by the following:

$$\text{mean value} + (2*\text{standard deviation}) < \text{Outlier} < \text{mean value} - (2*\text{standard deviation})$$

Statistical Analysis

Statistical analysis of the permeation and recovery data from the donor, surface, Stratum corneum, epidermis, dermis and receiver fluid was performed using SPSS. The recovery data was analyzed to confirm whether the variance of each group was equal using the Levene's test. If the data was of equal or unequal variance, the determined p value is either $p>0.05$ or $p \leq 0.05$, respectively. Subsequently, an independent T-test was used assuming equal (i.e. $p>0.05$) or unequal variance (i.e. $p<0.05$) and the statistical comparison was performed for the amount of Compound I recovered from the skin matrices. The comparison between the recovery of Compound I from the Stratum corneum, epidermis and dermis of the same formulations was analyzed for normality using the Shapiro-Wilk test to determine if the data was either parametric or non-parametric, where the determined p value was either $p>0.05$ or $p \leq 0.05$, respectively. If the data was parametric (i.e. normally distributed, p>0.05 determined using the Shapiro-Wilk test) the statistical comparison was performed using a one way ANOVA Tukey's HSD. However, if it was determined that the data was non-parametric (i.e. unequal variances p≤0.05 determined using the Shapiro-Wilk test) the statistical comparison of the data was carried out using a one way ANOVA with Post Hoc Tamhane.

Results

Small Scale Permeation/Penetration Experiment

The small scale permeation experiment was conducted using the following procedure:

Compound I in PEG-400 (SS1) and Compound I in PEG-400 (75% w/w) and Transcutol P (25% w/w) (SS2) were assessed, n=3 cells per solvent system using skin from a single donor (dermatomed human skin)

Dosage: ca. 6 mg (i.e. 10 mg/cm$^2$)

EtOH (20% v/v) in water was used as the receiver fluid

Receiver fluid samples were taken at t=0, 1, 2, 4, 6, 24, 30 and 48 h. Two sample volumes were investigated due to the low solubility of Compound I in potential receiver fluids; 200 μL and 1.5 mL.

Following the final time point Compound I was recovered from the donor compartment, surface, Stratum corneum, epidermis and dermis using tissue homogenization and solvent extraction (diluent: 90:10, EtOH: water).

The small scale experiment was used to confirm the protocol for the full scale permeation/penetration experiment. Compound I was not detected in the receiver fluid over the duration of the 48 h experiment irrespective of sample volume.

Figure 2:
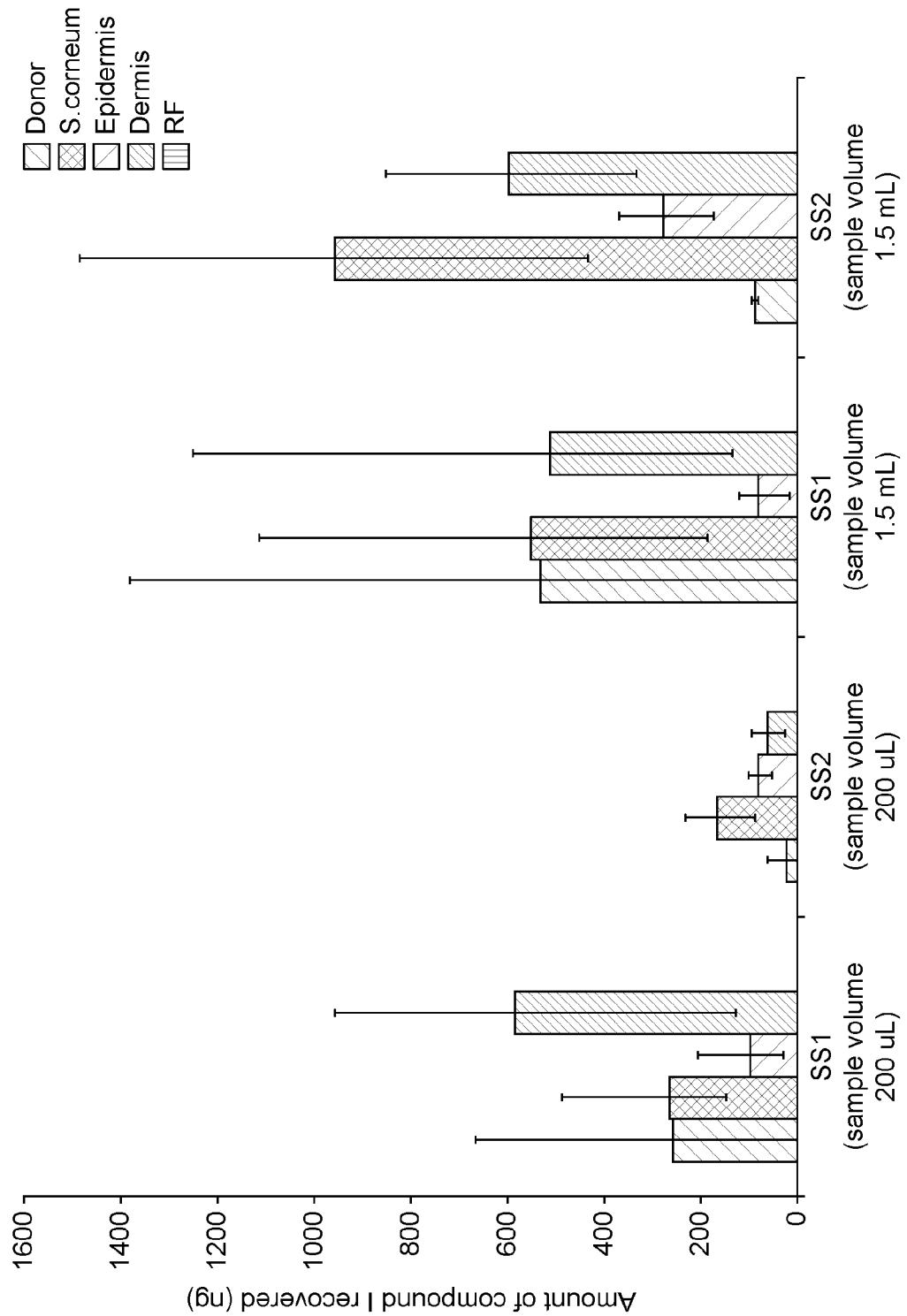
FIG. 2 shows the same data as FIG. 1, but with the amount recovered from the surface removed for ease of data interpretation.

The values for the recovery of Compound I following the application of solvent systems SS1 and SS2 are illustrated in FIG. 1 with the amount recovered from the surface removed in FIG. 2 for ease of data interpretation. For each solvent system applied the total recovery of Compound I ranged from 90.00-109.72% of the applied dose. The highest amount of Compound I was recovered from the solvent system remaining on the surface. Compound I was also recovered from the Stratum corneum, epidermis and dermis in similar amounts.

Full Scale In Vitro Permeation and Penetration Experiment

The permeation and penetration of Compound I from two solvent systems was assessed using abdominal skin from three skin donors. The mean cumulative amount (ng/cm$^2$) of Compound I permeated following the application of the solvent systems through dermatomed skin was plotted against time (h). The solvent systems were: Compound I in PEG-400 (FSS1) and Compound I in PEG-400 (60% w/w), Arlasolve DMI (15% w/w) and Transcutol P (25% w/w) (FSS2). The amount of Compound I (ng, mean+SEM) from the donor, surface, Stratum corneum, epidermis, dermis and receiver fluid were presented from all three skin donors.

Figure 3:
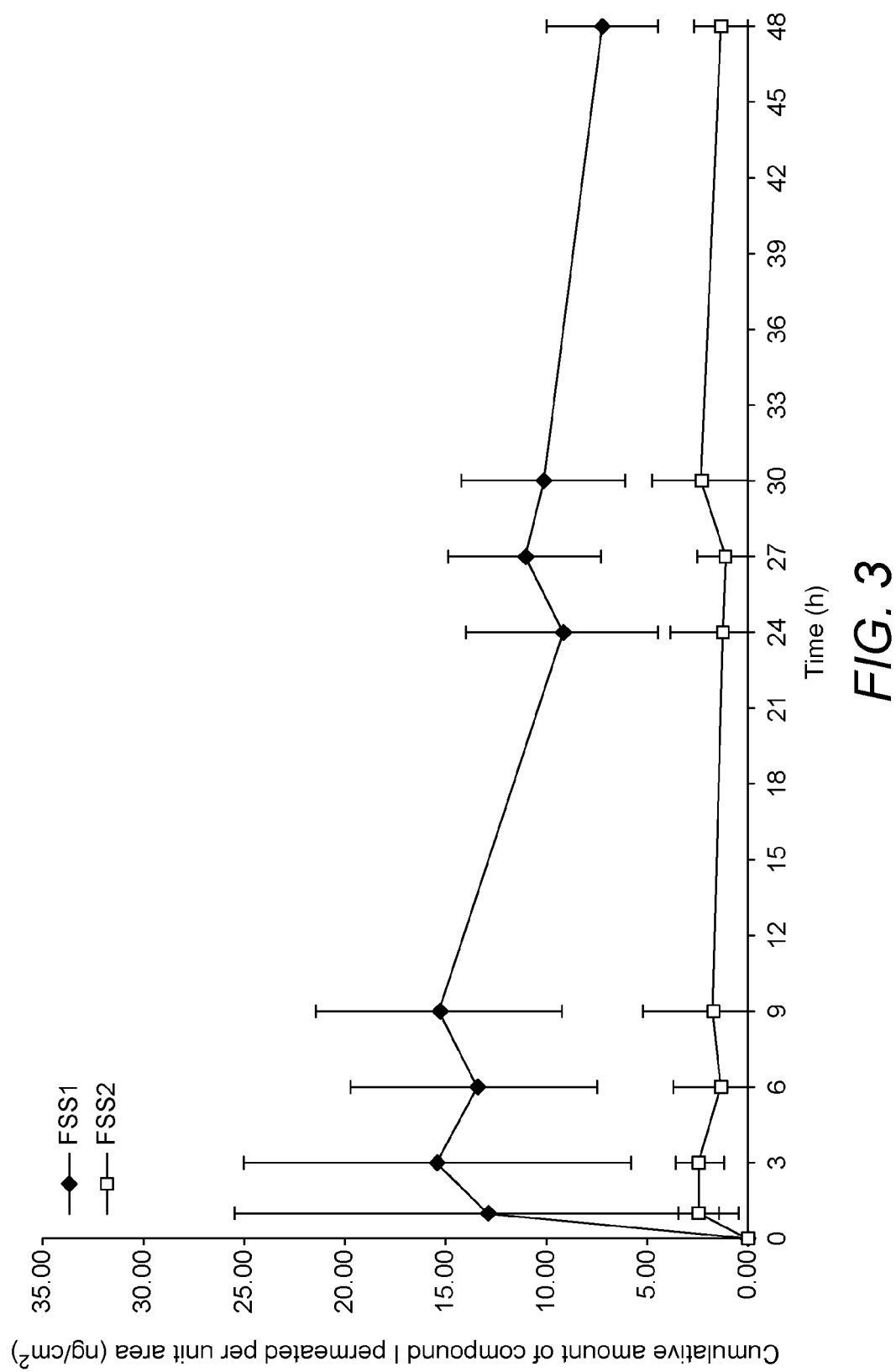
FIG. 3 shows the cumulative amount of Compound I in the receiver compartment per unit area (ng/cm$^2$) over a 48 h experimental period following the application of the solvent systems FSS1 and FSS2. Each point represent the mean level of Compound I±SD detected in the receiver fluid across skin from three donors, n=9-10.
Figure 4:
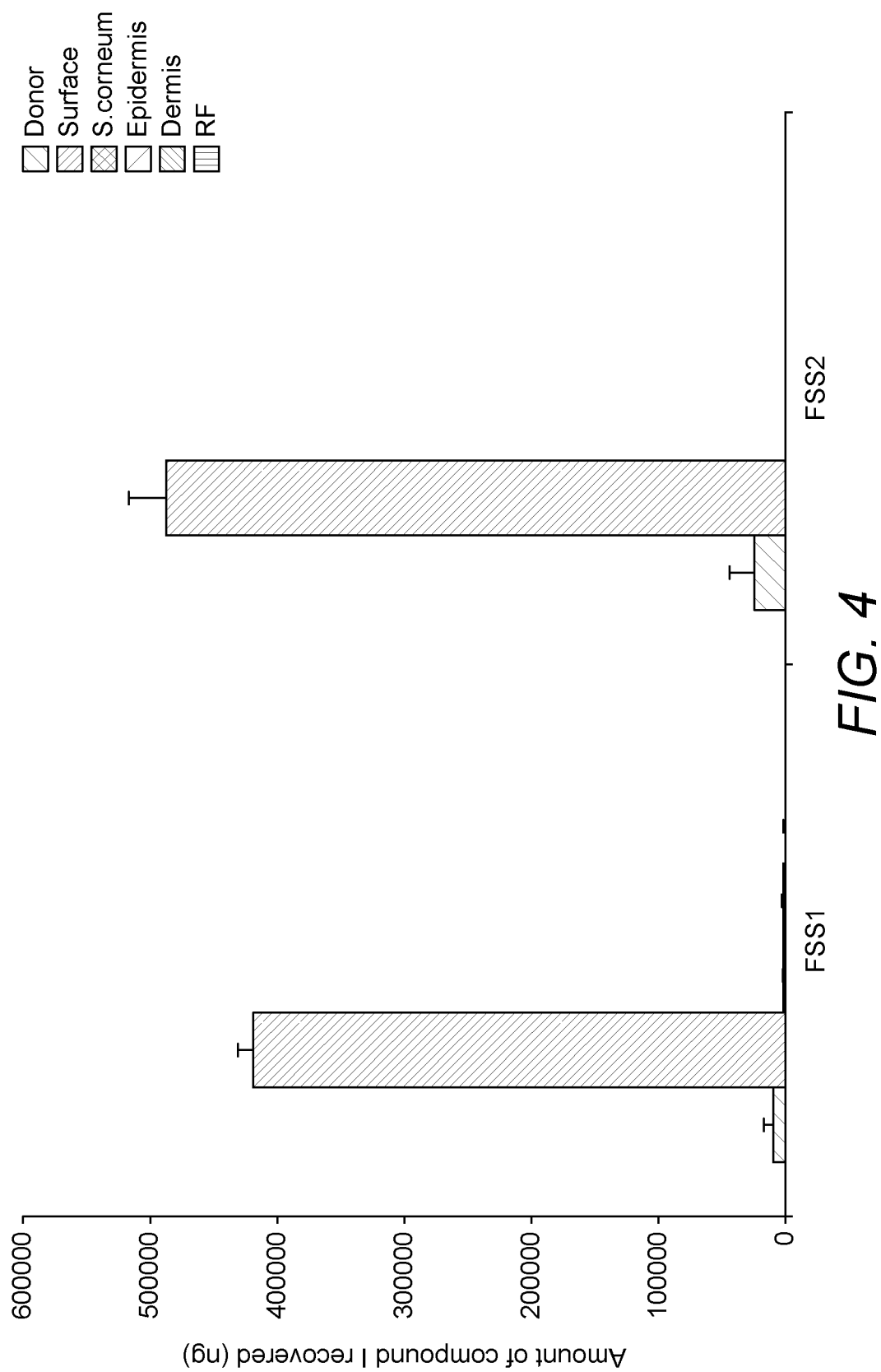
FIGS. 4 and 5 show the in vitro penetration of Compound I from the solvent systems (FSS1 and FSS2), across dermatomed abdominal skin from three donors. Each point represents the mean level of Compound I recovered±SEM, n=9-10.
Figure 5:
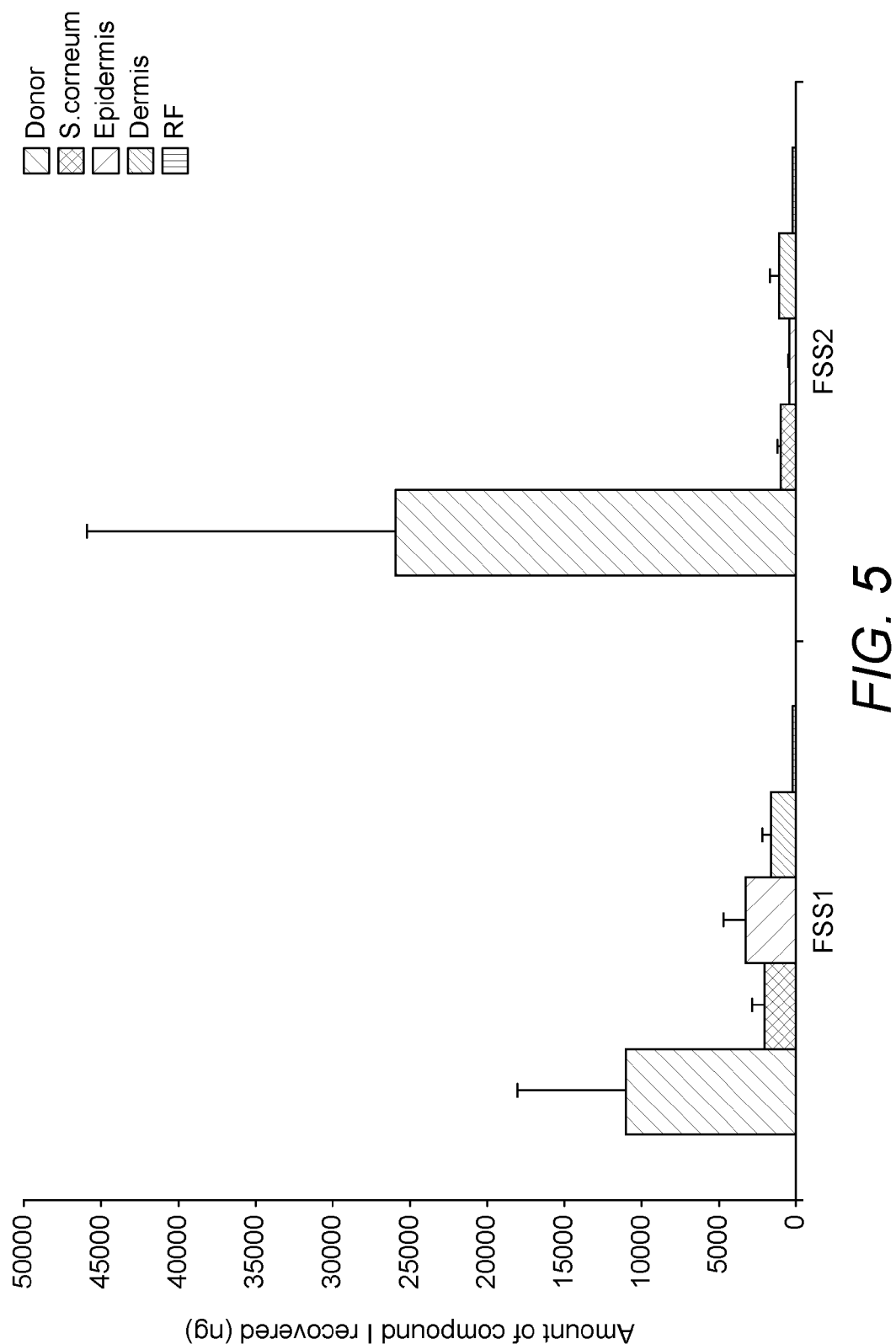

The in vitro permeation of Compound I from the two solvent systems (FSS1 and FSS2), across dermatomed abdominal skin from three donors over a 48 h experimental period is illustrated in FIG. 3. Permeation of Compound I was observed at low levels from both solvent systems over the 24 h experimental period with Compound I which was first detected in the receiver fluid after 1 h post application of the solvent systems (FSS1 and FSS2). The permeation profiles of Compound I for both solvent systems followed a similar trend with Compound I present in the receiver fluid at t=1 h followed by a plateau, the decrease towards the end of the profile was within error and thought to be a result of the low levels of Compound I being quantified and donor to donor variability. Despite the low levels of Compound I detected in the receiver fluid the permeation of Compound I following application of FSS1 was observed to be significantly higher (p<0.05) than the permeation of Compound I following the application of FSS2. The in vitro penetration of Compound I from the solvent systems (FSS1 and FSS2), across dermatomed abdominal skin from three donors is illustrated in FIGS. 4 and 5. The recovery of Compound I following the final time point was observed to be 101.47% and 87.39% of the applied dose for solvent systems FSS1 and FSS2, respectively. Compound I was recovered in the highest amounts from the surface of the skin following the application of FSS1 and FSS2, were between ca. 82% (FFS2)-ca. 97% (FSS1) of the applied dose was recovered.

For ease of data interpretation the amount of Compound I recovered from the surface has been removed in FIG. 5 to highlight the recovery of Compound I from the Stratum corneum, epidermis, dermis and receiver fluid between the solvent systems (FSS1 and FSS2). The amount of Compound I recovered following the application of FSS1 was highest (based on mean amounts) in the epidermis (3281±1435 ng)>Stratum corneum (1976±729 ng)>dermis (1593±609 ng)>receiver fluid (4.67±0.58 ng). The amount of Compound I recovered from the skin layers and receiver fluid following the application of FSS2 was lower (although no significant difference was observed between the skin layers, p>0.05, the receiver amount of Compound I recovered from the receiver fluid was significantly lower (p<0.05)) than the amount recovered following the application of FSS1. The rank order of Compound I recovered from the skin matrices was different to that observed with FSS1 with the highest amount (based on average amount) of Compound I recovered from the dermis (1126±543 ng)>Stratum corneum (931±310 ng)>epidermis (352±113 ng)>receiver fluid (0.89±0.27 ng). However, the difference in rank order was not considered an issue, as the levels recovered in the Stratum corneum, epidermis and dermis were not significantly different (p>0.05) for each solvent system.

The approximate concentration of Compound I within the epidermis and dermis was calculated using the following procedure:

a. The thickness of the epidermis and partial dermis were assumed to be between 30-130 and 250-350 μm, respectively (a range of skin thickness were used to provide the best and worst case scenario for the level of Compound I detected in the epidermis).

b. The area of the skin used was ca. 0.6 cm$^2$ and therefore the volume of the epidermis and partial dermis were 0.0018-0.0078 and 0.015-0.021 cm$^3$, respectively.

c. Assuming the density of the skin is 1 and that 1 cm$^3$=1 g the weight of the epidermis and partial dermis would be 0.0018-0.0078 and 0.015-0.021 g, respectively.

d. The total amount of Compound I recovered from the epidermis and partial dermis were then divided by the mass to obtain and approximate amount (ng/g) of Compound I recovered.

e. The amount recovered (ng/g) was subsequently divided by the molecular weight (823.34 Da) to provide a concentration in nanomoles/g which was subsequently converted to micromoles/kg (micromolality) of Compound I recovered from the epidermis and dermis (equivalent to micromolarity (μmol/L; μM) when assuming the density of the skin is 1 g/cm$^3$).

The results of the calculation are summarized in Table 2. Compound I is a sub-low nanomolar inhibitor of cPLA2α activity in cellular and enzymatic assays. The concentrations detected in the epidermis and dermis is indicative that they are sufficient to significantly inhibit cPLA2α biological activity at these sites.

Table 2. Concentration range of Compound I (μM) in the epidermis and dermis (based on average amounts and a range of skin thickness) following application of FSS1 and FSS2 at the 48 h time point. Values represent a range based on skin thickness and average amount recovered, n=9-10.

| Skin layer | Average concentration (μM) | |
|---|---|---|
| | FSS1 | FSS2 |
| Epidermis | 511-2214 | 55-238 |
| Dermis | 92-129 | 65-91 |

Example 3—Effect on PMA-Induced Inflammation in Mice

Phorbol 12-myristate 13-acetate (PMA) is commonly used to induce inflammation and oedema of the skin of laboratory animals as a preclinical inflammation model.

In the present example PMA was dissolved in a 10% ethanol solution to a final concentration of 0.4 μg per μl. A 10 μl was applied to the ears of Balb/C laboratory mice 1 hour after topical application of 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid (Compound I) in a 10% ethanol solution at either 0.3% or 3% w/w. As a negative control the vehicle was applied without the active compound. Positive controls were indomethacin (a non-steroidal anti-inflammatory drug) and CAY10650 (a known cPLA$_2$α inhibitor).

Figure 6:
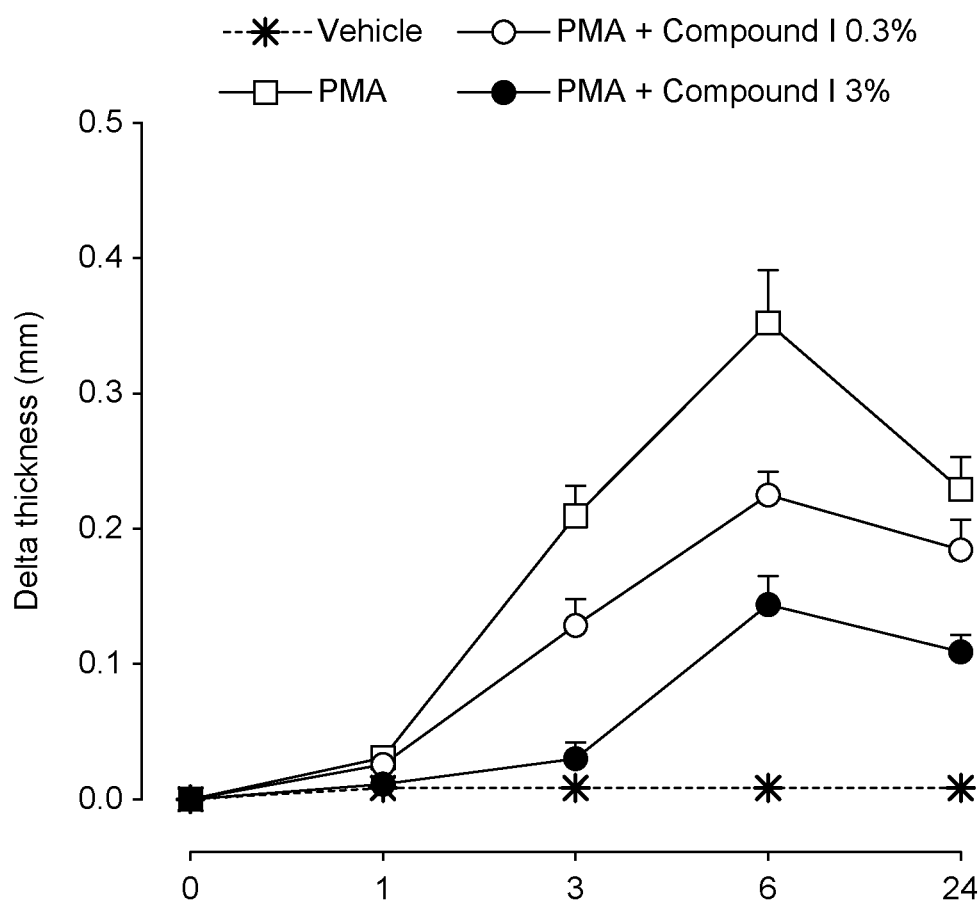
FIG. 6 shows the change in ear thickness over time (in hours after PMA application) for different doses of Compound I.

The level of oedema was monitored by measurement of ear thickness by calliper at intervals of 1, 3, 6 and 24 hours FIG. 6 shows the change in ear thickness over time (in hours after PMA application) for different doses of 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid (Referenced as Compound I).

Figure 7:
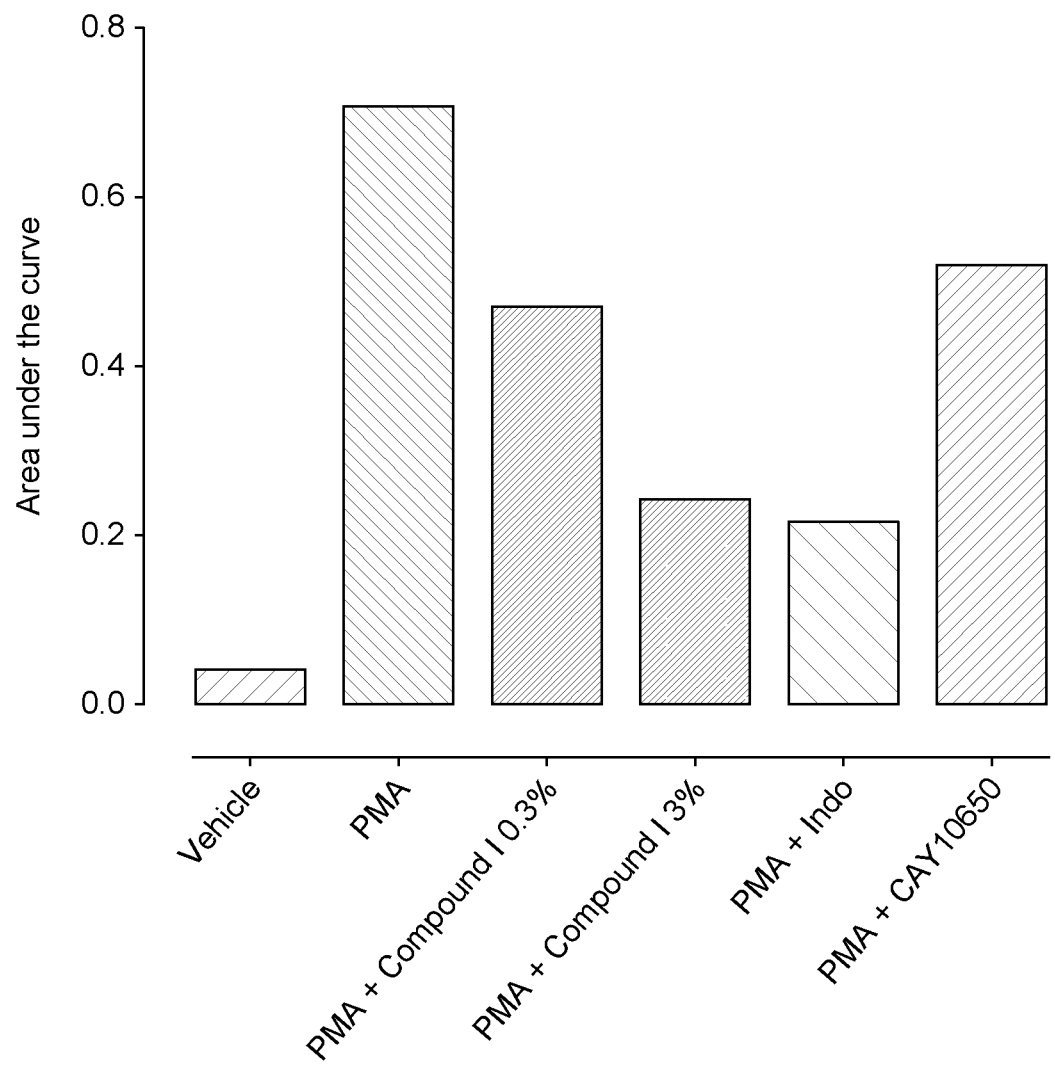
FIG. 7 shows a comparison of Compound I with other compounds.

FIG. 7 shows a comparison of 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid (Referenced as Compound I) with other compounds.

Topically applied 3-{4-[2-{5-chloro-1-(diphenylmethyl)-2-[2-({[2-(trifluoromethyl)benzyl]sulfonyl}amino)ethyl]-1H-indol-3-yl}ethyl]sulfonyl}phenyl}propanoic acid was found to show dose-dependent reduction in PMA-mediated skin oedema with efficacy comparable to orally-dosed indomethacin.

This demonstrates that the drug is effective in vivo when administered topically.

Example 4—Preparation of PEG Based Ointments

Several ointments as described in Table 3 were prepared according to the following procedure:
(i) PEG-400 was weighed into a suitably sized glass container.
(ii) The Compound I was weighed (where applicable) into a weigh boat and then transferred into the system from Step (i) and stirred until complete dissolution was observed.
(iii) The following excipients (where applicable), propylene glycol, ethanol, water and glycerol were sequentially weighed into the container from Step (ii), a magnetic follower was inserted and the contents stirred until the solution was observed to be visually homogenous.
(iv) PEG 400 was weighed into a separate suitably sized glass container and heated in a water bath previously calibrated at 65° C.
(v) PEG 400 was stirred until a clear melt was observed at which point it was added to the solvent system (step (iii)) which had been heated to 61° C.
(vi) The formulation (step (iv)) was stirred until visually mixed and then removed from the water bath.
(vii) The formulation was mixed until it reached ambient temperature.

TABLE 3

Composition (% w/w) of ointment formulations

| Ointment name | PEG-400 | PG | Ethanol | Water | Glycerol | PEG-4000 | Compound I | TOTAL |
|---|---|---|---|---|---|---|---|---|
| O2 | 69.9 | 5.1 | 0 | 5 | 0 | 17 | 3 | 100 |
| O2X | 69.9 | 5.1 | 0 | 0 | 5 | 17 | 3 | 100 |
| O4 | 50 | 19 | 0 | 5 | 5 | 20 | 1 | 100 |
| O4v4 | 52.5 | 16.5 | 0 | 5 | 5 | 20 | 1 | 100 |
| O4v4E | 52.5 | 16.5 | 5 | 5 | 0 | 20 | 1 | 100 |
| O5v2 | 45 | 25 | 0 | 10 | 0 | 19.7 | 0.3 | 100 |
| O5v2E | 45 | 25 | 5 | 5 | 0 | 19.7 | 0.3 | 100 |
| O5X | 45 | 25 | 0 | 0 | 10 | 19.7 | 0.3 | 100 |
| O5EX | 45 | 25 | 5 | 0 | 5 | 19.7 | 0.3 | 100 |
| O7 | 59.9 | 0 | 10 | 5 | 5.1 | 17 | 3 | 100 |
| O8 | 59.9 | 5 | 10 | 0 | 5.1 | 17 | 3 | 100 |

Example 5—Preparation of Cream and Lotion Formulations

Cream and lotion formulations as described in Tables 4, 5 and 6 were prepared as described below:
(i) PEG-400 was weighed into a suitably sized glass container.
(ii) Compound I was weighed (where applicable) into a weigh boat and then transferred into the system from Step (i) and stirred overnight.
(iii) The remaining aqueous phase excipients were weighed into a container from Step (ii) and the contents stirred.
(iv) The gelling agent (if applicable) was added to the vial from Step (iii) and homogenized for 30 s or until the complete dispersion of the gelling agent was observed.
(v) In a separate suitably sized glass container the oil phase excipients were weighed and the oil phase heated in a water bath previously calibrated at 65° C.
(vi) The oil phase was stirred until a clear melt was observed.
(vii) When a clear melt of the oil phase from Step (iii) was observed the aqueous phase from Step (v) was preheated for a maximum of 5 min in a water bath previously calibrated at 61° C.
(viii) The oil phase was slowly transferred into the aqueous phase and the formulation from Step (vii) was homogenized on the maximum speed setting (10,000 RPM) for 2 min. Prior to homogenizing the formulation the homogeniser head was pre-warmed.

(ix) The formulation was then stirred by hand until it had cooled to room temperature.

TABLE 4

Example Tween/Span Creams

| Excipient | Composition (% w/w) | | |
|---|---|---|---|
| | Tween/Span cream 1 | Tween/Span cream 2 | Tween/Span cream 4 |
| Ethanol | 5 | — | 5 |
| Water | 19.7 | 19.7 | 11.5 |
| PEG-400 | 36 | 41 | 43.5 |
| Transcutol P | 15 | — | 15 |
| Arlasolve DMI | — | 15 | — |
| Benzyl alcohol | 2 | 2 | 2 |
| Phenoxyethanol | — | — | — |
| Carbopol 980 | — | — | — |
| Tween 60 | 5 | 5 | 5 |
| Span 60 | 2 | 2 | 2 |
| White soft paraffin | — | — | — |
| Liquid paraffin | — | — | — |
| Cetostearyl alcohol | 5 | 5 | 5 |
| Cetomacrogol 1000 | — | — | — |
| Crodamol GTCC | 10 | 10 | 10 |
| Compound I | 0.3 | 0.3 | 1 |
| TOTAL | 100 | 100 | 100 |

TABLE 5

Examples of cream (cetomacrogol) formulations

| Excipient | Composition (% w/w) | | | | | | | |
|---|---|---|---|---|---|---|---|---|
| | Cream 1 | Cream 2 | Cream 3 | Cream 4 | Cream 6 | Cream 7 | Cream 7PE | Cream 9 |
| Ethanol | — | 5 | 5 | — | — | 5 | 5 | 5 |
| Water | 19.7 | 15.7 | 5 | 19.5 | 19.7 | 13.7 | 13.7 | 10.5 |
| PEG-400 | 41 | 33 | 38 | 41 | 51.7 | 36 | 37 | 43.5 |
| Transcutol P | — | 15 | 15 | — | — | 15 | 15 | 15 |
| Arlasolve DMI | 15 | — | — | 15 | 15 | — | — | — |
| Benzyl alcohol | 2 | 2 | 2 | 2 | 2 | 2 | — | 2 |
| Phenoxyethanol | — | — | — | — | — | — | 1 | — |
| Carbopol 980 | — | — | — | 0.5 | 0.5 | 1 | 1 | 1 |
| Tween 60 | — | — | — | — | — | 5 | 5 | — |
| White soft paraffin | 8 | 6 | 10 | 8 | 1 | 8 | 8 | 8 |
| Liquid paraffin | 6 | 10 | 10 | 6 | — | 6 | 6 | 6 |
| Cetostearyl alcohol | 6 | 10 | 12 | 6 | 3 | 6 | 6 | 6 |
| Cetomacrogol 1000 | 2 | 3 | 3 | 2 | 1.8 | 2 | 2 | 2 |
| Crodamol GTCC | — | — | — | — | 5 | — | — | — |
| Compound I | 0.3 | 0.3 | — | — | 0.3 | 0.3 | 0.3 | 1 |
| TOTAL | 100 | 100 | 100 | 100 | 100 | 100 | 100 | 100 |

TABLE 6

Example lotion formulations

| Excipient | Composition (% w/w) | | | | | | | |
|---|---|---|---|---|---|---|---|---|
| | Ceto-macrogol lotion 1 | Ceto-macrogol lotion 2 | Ceto-macrogol lotion 3 | Tween/Span lotion 4 | Tween/Span lotion 5 | Ceto-macrogol lotion 6 | Myrj/GMS lotion 7 | Myrj/GMS lotion 8 |
| Water | 19.5 | 19.5 | 19.5 | 20 | 20 | 20 | 20 | 19.2 |
| PEG-400 | 41 | 41 | 41 | 48 | 49 | 51.7 | 51.75 | 52.25 |
| Arlasolve DMI | 15 | 15 | 15 | 15 | 15 | 15 | 15 | 15 |
| Benzyl Alcohol | 2 | 2 | 2 | 2 | 2 | 2 | 2 | 2 |
| Carbopol 980 | — | — | — | — | — | 0.5 | 0.5 | 0.5 |
| White soft paraffin | 4 | — | — | — | — | 1 | — | — |
| Liquid paraffin | 9.5 | 13.5 | 16.3 | — | — | — | — | 5 |
| Crodamol GTCC | - | - | - | 5 | 5 | 5 | 5 | — |
| Cetostearyl alcohol | 7.2 | 7.2 | 5 | 3 | 2 | 3 | 3 | 3 |
| Cetomacrogol 1000 | 1.8 | 1.8 | 1.2 | — | — | 1.8 | — | — |
| Tween 60 | — | — | — | 5 | 5 | — | | |
| Span 60 | — | — | — | 2 | 2 | — | | |
| Myrj S40 | — | — | — | — | — | — | 2 | 2 |
| GMS | — | — | — | — | — | — | 0.75 | 0.75 |
| Compound I | 0 | 0 | 0 | 0 | 0 | 0 | 0 | 0.3 |
| TOTAL | 100 | 100 | 100 | 100 | 100 | 100 | 100 | 100 |

Example 6—Preparation of Gel Formulations

Several gel formulations as described in Table 7 were prepared as follows:

Gel Formulations
(i) PEG-400 was weighed into a suitably sized glass container.
(ii) Compound I was weighed (where applicable) into a weigh boat and then transferred into the system from Step (i) and stirred until complete dissolution was observed.
(iii) The following excipients (ethanol, water, propylene glycol, Transcutol P, Arlasolve DMI, benzyl alcohol and phenoxyethanol, where applicable) were sequentially weighed into a the glass vial from Step (ii).
(iv) A magnetic follower was inserted into the vial from Step (iii) and the contents of the vial were stirred until visually homogenous.
(v) The gelling agent (HPC/Carbopol 980) was weighed into a weigh boat and transferred slowly (mitigating the risk of agglomeration of the gelling agent) to the vial from Step (iv) under constant stirring.
(vi) For Carbopol based gels the pH was checked to ensure it was ca. pH 6, where no pH adjustment would be required.
(vii) The formulations were stirred until complete hydration of the gelling agent was observed.

Emulsfied Gel Formulations
(i) PEG-400 was weighed into a suitably sized glass container.
(ii) Compound I was weighed (where applicable) into a weigh boat and then transferred into the system from Step (i) and stirred until complete dissolution was observed.
(iii) The following excipients (ethanol, water, propylene glycol, Transcutol P, Arlasolve DMI, benzyl alcohol, phenoxyethanol and poloxamer 407, where applicable) were sequentially weighed into the glass vial from Step (ii).
(iv) A magnetic follower was inserted into the vial from Step (iii) and the contents of the vial were stirred until visually homogenous.
(v) The gelling agent (Carbopol 980) was weighed into a weigh boat and transferred slowly (mitigating the risk of agglomeration formation) to the vial from Step (iv) under constant stirring.
(vi) The pH was checked to ensure it was ca. pH 6, where no pH adjustment would be required.
(vii) Cyclomethicone was weighed into the glass vial from Step (v) and the system was homogenized for 2 min at 10,000 RPM until complete dispersion of the cyclomethicone was observed.
(viii) The formulations were subsequently stirred until complete hydration of the gelling agent was observed.

TABLE 7

Example gel formulations

| Excipient (% w/w) | Ethanol | Water | PEG-400 | PG | Transcutol P | Arlasolve DMI | Benzyl alcohol | Phenoxyethanol | Cyclomethicone | IPM | Poloxamer 407 | HPC HF | Carbopol 980 | Compound I | TOTAL |
|---|---|---|---|---|---|---|---|---|---|---|---|---|---|---|---|
| Gel 1 (HPC) | 10 | 10 | 51 | — | 22 | — | 2 | — | — | — | — | 2 | — | 3 | 100 |
| Gel 1 (C980) | 10 | 10 | 51 | — | 22 | — | 2 | — | — | — | — | — | 2 | 3 | 100 |
| Gel 1v2 (C908) | 10 | 10 | 52 | — | 22 | — | 2 | — | — | — | — | — | 1 | 3 | 100 |
| Gel 1v3 (C980) | 10 | 10 | 51.5 | — | 22 | — | 2 | — | — | — | — | — | 1.5 | 3 | 100 |
| Gel 4 (HPC) | 10 | 9.5 | 59 | — | — | 15 | 2 | — | — | — | — | 1.5 | — | 3 | 100 |
| Gel 4v3 (C980) | 10 | 9.5 | 59 | — | — | 15 | 2 | — | — | — | — | — | 1.5 | 3 | 100 |
| Gel 7v3 (C980) | 10 | 19 | 26.5 | — | 25 | 15 | 2 | — | — | — | — | — | 1.5 | 1 | 100 |
| Gel 7PE | — | 19 | 27.5 | 10 | 25 | 15 | — | 1 | — | — | — | — | 1.5 | 1 | 100 |
| Gel 7BA | — | 19 | 26.5 | 10 | 25 | 15 | 2 | — | — | — | — | — | 1.5 | 1 | 100 |
| Emulsified gel 1 (IPM) | 10 | 11.5 | 40.5 | 5 | 15 | — | 2 | — | — | 13 | 1 | — | 1 | 1 | 100 |
| Emulsified gel 1 (cyclomethicone) | 10 | 11.5 | 40.5 | 5 | 15 | — | 2 | — | 13 | — | 1 | — | 1 | 1 | 100 |
| Emulsified gel 1v2 | 10 | 11.25 | 40.5 | 5 | 15 | — | 2 | — | 13 | — | 1 | — | 1.25 | 1 | 100 |

While the invention has been described in detail and with reference to specific embodiments thereof, it will be apparent to one of skill in the art that various changes and modifications can be made therein without departing from the spirit and scope thereof. Moreover, all embodiments described herein are considered to be broadly applicable and combinable with any and all other consistent embodiments, as appropriate.

The invention claimed is:

1. A pharmaceutical composition for topical administration comprising between 0.01% and 10% (w/w) of a compound of formula I:

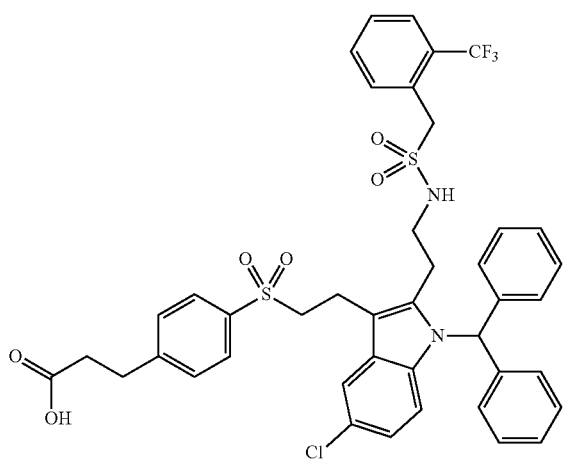 [SMILES: O=C(O)CCc1ccc(S(=O)(=O)CCc2c(CCNS(=O)(=O)Cc3ccccc3C(F)(F)F)n(C(c3ccccc3)c3ccccc3)c3ccc(Cl)cc23)cc1]

or pharmaceutically acceptable salts thereof,
wherein the composition is in a form for topical administration,
wherein the composition comprises a solvent, a co-solvent, a penetration enhancer, and water.

2. The composition according to claim 1, wherein the compound of formula I or pharmaceutically acceptable salt thereof is present at from 0.3% to 3%.

3. The composition according to claim 1, wherein the compound of formula I or pharmaceutically acceptable salt thereof is present at 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10% (w/w).

4. The composition according to claim 1, wherein the composition is in a form selected from ointments, gels, creams, lotions, oil-in-water emulsions, water-in-oil emulsions, microemulsions, foams, sprays, mousses, patches, powders, pastes, and medicated plasters.

5. The composition of claim 4, wherein the composition is in the form of an ointment that comprises 69.9% (w/w) PEG-400, 5.1% (w/w) propylene glycol, 5% (w/w) water, 17% (w/w) PEG-4000, and 3% (w/w) of the compound of formula I.

6. The composition of claim 4, wherein the composition is in the form of an ointment that comprises 59.9% (w/w) PEG-400, 10% (w/w) ethanol, 5% (w/w) water, 5.1% (w/w) glycerol, 17% (w/w) PEG-4000, and 3% (w/w) of the compound of formula I.

7. The composition according to claim 1 where the composition also comprises additional therapeutic agents.

8. The composition of claim 1, further comprising an emulsifier.

9. The composition of claim 1 further comprising a viscosity-increasing agent.

10. The pharmaceutical composition for topical administration of claim 1 for use in therapy.

11. The pharmaceutical composition for topical administration of claim 1 for use in treating inflammation and/or oedema in a patient in need thereof.

12. The pharmaceutical composition for topical administration of claim 11 for use in treatment of dermal inflammatory diseases or conditions.

13. The composition for use of claim 12, wherein the dermal inflammatory disease or condition is a cytosolic phospholipase $A_2\alpha$-dependent or cytosolic phospholipase $A_2\alpha$-mediated disease or condition.

14. The composition for use of claim 12, wherein the dermal inflammatory disease or condition is selected from the group comprising scarring, dermatitis, a proliferative disease or condition, a mast cell disease or condition, a burn or contact with an allergen and/or an irritant.

15. The composition for use of claim 12, wherein the dermal inflammatory disease or condition is selected from the group comprising atopic dermatitis, bullous disorders, collagenoses, psoriasis, psoriatic lesions, seborrheic dermatitis or contact dermatitis, eczema, urticaria, pruritus, rosacea, prurigo nodularis, hypertrophic scarring, keloid scar formation, scleroderma, Folliculitis keloidalis nuchae, Kawasaki Disease, Sjögren-Larsson Syndrome, Grover's disease, a first degree burn, a second degree burn, a third degree burn, a fourth degree burn, cutaneous mucinosis, solar keratosis, squamous cell carcinoma or melanoma, asteatotic eczema, discoid eczema, hand eczema, gravitational/varicose eczema, eczematous drug eruptions, lichen simplex, lichen sclerosus, lichen planus Irritant, allergic contact dermatitis, photoallergic/photoaggravated dermatitis, infective (secondary to bacterial/viral/fungal infection) dermatitis, pruritic diseases including those associated with chronic systemic disorders such as uremic pruritus, cholestatic pruritus, adult blaschkitis, aquadynia, aquagenic pruritus, balsam of Peru, biliary pruritus, brachioradial pruritus, drug-induced pruritus, hydroxyethyl starch-induced pruritus, itchy points, lichen simplex chronicus, neurodermatitis, prion pruritus, prurigo, prurigo pigmentosa, prurigo simplex, pruritus ani, pruritus scroti, pruritus vulvae, puncta pruritica, referred itch, renal pruritus, scalp pruritus, senile pruritus, xerotic eczema, itch associated with HIV infection, T-cell lymphoma, Sezary syndrome and mycosis fungoides.

16. The composition for use of claim 12, wherein the dermal inflammatory disease or condition is selected from atopic dermatitis and psoriasis.

17. The composition according to claim 1 wherein the composition comprises additional therapeutic agents.

* * * * *